US009907809B2

(12) United States Patent
Phillips et al.

(10) Patent No.: US 9,907,809 B2
(45) Date of Patent: Mar. 6, 2018

(54) ANTIVIRAL SUPPLEMENT FORMULATIONS

(71) Applicant: Vymedic, LLC, Englewood, CO (US)

(72) Inventors: Kenneth E. Phillips, Tulsa, OK (US); Cynthia A. Winning, Parker, CO (US)

(73) Assignee: Vymedic, LLC, Englewood, CO (US)

( * ) Notice: Subject to any disclaimer, the term of this patent is extended or adjusted under 35 U.S.C. 154(b) by 0 days.

(21) Appl. No.: 14/681,817

(22) Filed: Apr. 8, 2015

(65) Prior Publication Data

US 2015/0272974 A1 Oct. 1, 2015

Related U.S. Application Data

(63) Continuation of application No. 12/609,120, filed on Oct. 30, 2009, now Pat. No. 9,034,834.

(60) Provisional application No. 61/111,234, filed on Nov. 4, 2008.

(51) Int. Cl.

| A61K 31/7048 | (2006.01) |
| A61K 31/7028 | (2006.01) |
| A61K 31/70 | (2006.01) |
| A61K 31/185 | (2006.01) |
| A61K 31/198 | (2006.01) |
| A61K 31/221 | (2006.01) |
| A61K 31/375 | (2006.01) |
| A61K 31/4415 | (2006.01) |
| A61K 31/513 | (2006.01) |
| A61K 45/06 | (2006.01) |
| A61K 31/145 | (2006.01) |
| A61K 31/44 | (2006.01) |
| A61K 31/455 | (2006.01) |

(52) U.S. Cl.
CPC ........ *A61K 31/7028* (2013.01); *A61K 31/145* (2013.01); *A61K 31/185* (2013.01); *A61K 31/198* (2013.01); *A61K 31/221* (2013.01); *A61K 31/375* (2013.01); *A61K 31/44* (2013.01); *A61K 31/4415* (2013.01); *A61K 31/455* (2013.01); *A61K 31/513* (2013.01); *A61K 31/7048* (2013.01); *A61K 45/06* (2013.01)

(58) Field of Classification Search
CPC .............. A61K 31/7028; A61K 31/198; A61K 31/375; A61K 31/145; A61K 31/44; A61K 31/455
USPC ................... 514/27, 25; 535/4.1, 8
See application file for complete search history.

(56) References Cited

U.S. PATENT DOCUMENTS

| 4,424,232 | A | 1/1984 | Parkinson |
| 5,278,189 | A | 1/1994 | Rath et al. |
| 5,626,883 | A | 5/1997 | Paul |
| 5,650,418 | A | 7/1997 | Rath et al. |
| 5,719,133 | A | 2/1998 | Schmidl et al. |
| 6,037,375 | A | 3/2000 | Sakamoto et al. |
| 6,316,008 | B1 | 11/2001 | Godfrey |
| 6,362,225 | B1 | 3/2002 | Andreakos |
| 6,455,061 | B2 | 9/2002 | Richardson |
| 6,632,445 | B2 | 10/2003 | Richardson et al. |
| 6,939,860 | B2 | 9/2005 | Netke et al. |
| 6,974,833 | B2 | 12/2005 | Rath |
| 7,041,699 | B2 | 5/2006 | Netke et al. |
| 7,351,715 | B2 | 4/2008 | Richardson et al. |
| 7,431,942 | B2 | 10/2008 | Shimizu et al. |
| 2002/0151599 | A1 | 10/2002 | Buchholz et al. |
| 2003/0064104 | A1 | 4/2003 | Stillman |
| 2003/0170319 | A1 | 9/2003 | Netke et al. |
| 2004/0067890 | A1 | 4/2004 | Gupta |
| 2005/0032715 | A1 | 2/2005 | Netke et al. |
| 2005/0281794 | A1 | 12/2005 | Rath |
| 2006/0142212 | A1 | 6/2006 | Netke et al. |
| 2007/0134320 | A1 | 6/2007 | Lowder |
| 2007/0160591 | A1* | 7/2007 | Lane ..................... A23L 33/175 424/94.1 |
| 2007/0212426 | A1 | 9/2007 | Rath et al. |
| 2008/0038367 | A1* | 2/2008 | Saloum ................ A61K 36/185 424/617 |

FOREIGN PATENT DOCUMENTS

| EP | 0 799 578 A2 | 10/1997 |
| WO | 9215315 A1 | 9/1992 |
| WO | 2007106675 A2 | 1/2007 |
| WO | 2007057748 A2 | 5/2007 |
| ZA | 200 402 741 A | 10/2004 |

OTHER PUBLICATIONS

Axelrod et al., "Effects of Pantothenic Acid, Pyridoxine and Thiamine Deficiencies upon Antibody Formation to Influenza Virus PR-8 in Rats"; J. Nutrition, 72:325-330 (1980).
Barbour et al., "Alleviation of Histopathologic Effects of Avian Influenza Virus by a Specific Nutrient Synergy"; Intern. J. Appl. Res. Vet. Med., 5(1):9-16 (2007).
Becht, "Induction of an Arginine-rich Component During Infection with Influenza Virus"; J. Gen. Virol., 4:215-220 (1969).
Chorazy et al., "Taurine chloramine modulates cytokine production by human peripheral blood mononuclear cells"; Amino Acids, 23:407-413 (2002).
Extended European Search Report and Written Opinion dated Apr. 23, 2012 in 09825263.8.
Friedman, "Absorption and Utilization of Amino Acids"; CRC Press, vol. II, Ch. III, pp. 48-49, ISBN 0849360072 (1989).

(Continued)

*Primary Examiner* — Shaojia Anna Jiang
*Assistant Examiner* — Michael C Henry
(74) *Attorney, Agent, or Firm* — Merchant & Gould, P.C.

(57) ABSTRACT

The disclosure provides an oral antiviral supplement composition comprising a lysine, an ascorbic compound, a flavonoid glycoside, a threonine, and a pyridoxine. The disclosure also provides a method of reducing viral replication in a cell comprising treating a virus-infected cell with a composition of the disclosure. The disclosure further provides a method for the treatment and prophylaxis of a viral infection in a patient comprising administering a composition of the disclosure.

21 Claims, 13 Drawing Sheets

(56) References Cited

OTHER PUBLICATIONS

Fuchs et al., EP0799578 A2 Oct. 8, 1997 (Machine English Translation).
Green et al., "Antioxidant role and subcellular location of hypotaurine and taurine in human neutrophils"; Biochimica et biophysica acta, 1073(1):91-97 (Jan. 23, 1991).
Griffith et al., "Success of L-lysine Therapy in Frequently Recurrent Herpes Simplex Infection. Treatment and prophylaxis"; Dermatologica, 175(4):183-190 (1987).
Grimble, "The effects of Sulfur Amino Acid Intake on Immune Function in Humans"; 5th Amino Acid Assessment Workshop, J. Nutrition, 136:1660S-1665S (2006).
Huxtable, "Taurine. Past, present, and future"; Adv Exp Med Biol. 403:641-650 (1996).
International Search Report and Written Opinion dated Feb. 1, 2010 in PCT/US09/62673.
Kim et al., "Flavanone Glycosides from Citrus junos and their Anti-Influenza Virus Activity"; Planta Med, 67(6):548-549 (Aug. 2001).
Lotan, "Humoral and Cellular Immune Response in Growing Rats Fed a 10% Gluten Diet"; Isr. J. Med. Sci. 25(8):437-441 (Aug. 1989).
Molecular Probes, Amplex® Red Neuraminidase (Sialidase) Assay Kit (A22178) (Product Information Rev. Oct. 1, 2004).
Roomi et al., "Modulation of N-methyl-N-nitrosurea induced mammary tumors in Sprague-Dawley rats by combination of lysine, praline, arginine, ascorbic acid, and green tea extract"; Breast Cancer Res., 7(3): R291-R295 (2005).
Sinha et al., "Taurine protects the antioxidant defence system in the erythrocytes of cadmium treated mice"; BMB Reports, 41(9):657-663 (2008).
Trakatellis et al., "Pyridoxine deficiency: new approaches in immunosuppression and chemotherapy"; Postgrad. Med. J., 73(864):617-622 (1997).
Williams et al., "Flavonoids: Antioxidants or Signalling Molecules?"; Free Radic. Biol. Med., 36(7):838-849 (2004).
Yeo et al., "Influenza A virus infection modulates expression of type IV collgenase in epithelial cells"; Arch. Virol., 144:1361-1370 (1999).
Dubber et al., "High-performance liquid chroomatographic determination of selected flavonols in Ginkgo biloba solid oral dosage forms.", J Phar Pharmaceut Sci, 2004, vol. 7, No. 3, pp. 303-309.
Boon et al., "In vitro effect of bioactive compounds on influenza virus specific B- and T-cell response", Jan. 1, 2002, URL: http://onlinelibrary.wiley.com/store/10.1046/j.1365-3083.2002.01014.x/asset/j.1365-3083.2002.01014.x.pdf?v=1&t=h0w9to5r&s=bb38381ad85acbac4df4fd9d379f86355d8fc27c, retrieved Apr. 11, 2012, 9 pages.
Braverman, "Taurine: The Seizure Fighter," The Healing Nutrients Within, 2003, pp. 131-143.
Braverman, "Threonine: The Immunity Booster," The Healing Nutrients Within, 2003, pp. 201-207.
Cai et al., "Inhibition of influenza infection by glutathione", Free Rad. Biol. And Med., (2003), vol. 34, No. 7, pp. 928-936.
CDC, Updated Interim Recommendations for the Use of Antiviral Medications in the Treatment and Prevention of Influenza for the 2009-2010 Season, (Sep. 22, 2009), URL: http://www.cdc.gov/h1n1flu/recommendations.htm.
Dharan et al., "Infections with Oseltamivir-resistant influenza A(H1N1) virus in the United States", JAMA, (2009), vol. 301, No. 10, pp. 1034-1041.
Hatakeyama et al., "Emergence of influenza B viruses with reduced sensitivity to neuraminidase inhibitors", JAMA, (2007), vol. 297, No. 13, pp. 1492-1493.
Hurt et al., "Zanamivir-resistant influenza viruses with a novel neuraminidase mutation," J. Virology, (200910), vol. 33, No. 20, pp. 10366-10373.
"Prevention & Control of Influenza—Recommendations of the Advisory Committee on Immunization Practices (ACIP) 2004", MMWR, (May 28, 2004), vol. 53, No. RR06, pp. 1-40.
Riley et al., "Secretion of matrix metalloproteinase-2, matrix metalloproteinase-9 and tissue inhibitor of metalloproteinases into the intrauterine compartments during early pregnancy", Molecul. Human Reprod, (1999), vol. 5, No. 4, pp. 676-381.
United States Pharmacopeia National Formulary USP, (1990), vol. XXII, pp. 1696-1697.

\* cited by examiner

Table 4. Neuraminidase Assay Test Compositions

| # | Material | M.W. (g/mol) | Wt (g) | Mols | 1 | 1,2 | 1,2,3 | 1,2,4 | 1,2,3,4 | 1,2,3,5 | 1,2,3,4,5 | 1,2,6 | 1,2,5 | 1,2,4,5 | 1,2,3,4,5,6 |
|---|---|---|---|---|---|---|---|---|---|---|---|---|---|---|---|
| 1 | L-Lysine HCl | 182.65 | 3.00 | 0.01642 | 3.00 | 3.00 | 3.00 | 3.00 | 3.00 | 3.00 | 3.00 | 3.00 | 3.00 | 3.00 | 3.00 |
| 5 | Threonine | 119.12 | 0.05 | 0.00042 | | | | | | 0.05 | 0.05 | | 0.05 | 0.05 | 0.05 |
|  | Ascorbic acid | 176.13 | 0.28 | 0.00159 | | 0.28 | 0.28 | 0.28 | 0.28 | 0.28 | 0.28 | 0.28 | 0.28 | 0.74 | 0.74 |
| 2 | Calcium ascorbate dihydrate | 426.34 | 0.64 | 0.0015 | | 0.64 | 0.64 | 0.64 | 0.64 | 0.64 | 0.64 | 0.64 | 0.64 | | |
|  | Niacinamide ascorbate | 298.25 | 0.30 | 0.00101 | | 0.30 | 0.30 | 0.30 | 0.30 | 0.30 | 0.30 | 0.30 | 0.30 | | |
|  | Ascorbyl palmitate | 414.54 | 0.05 | 0.00012 | | 0.05 | 0.05 | 0.05 | 0.05 | 0.05 | 0.05 | 0.05 | 0.05 | | |
| 3 | Hesperidin | 610.62 | 0.30 | 0.00049 | | | 0.30 | | 0.30 | 0.30 | 0.30 | | | | 0.30 |
|  | Rutin NF | 610.52 | 0.30 | 0.00049 | | | 0.30 | | 0.30 | 0.30 | 0.30 | | | | 0.30 |
| 4 | Pyridoxine HCl | 205.64 | 0.05 | 0.00024 | | | | 0.05 | 0.05 | | 0.05 | | | 0.05 | 0.05 |
| 6 | Taurine | 125.15 | 0.20 | 0.0016 | | | | | | | | 0.20 | | 0.20 | 0.20 |

FIGURE 7

ANTIVIRAL SUPPLEMENT FORMULATIONS

CROSS-REFERENCES TO RELATED APPLICATIONS

This application is a continuation application of U.S. patent application Ser. No. 12/609,120, filed Oct. 30, 2009, now U.S. Pat. No. 9,034,834, issued May 19, 2015, which claims the benefit of U.S. Provisional Application 61/111,234; filed Nov. 4, 2008, each of which is incorporated herein by reference in its entirety.

BACKGROUND OF THE DISCLOSURE

Field of the Disclosure

The disclosure provides oral antiviral supplement compositions comprising a lysine, an ascorbic compound, a flavonoid glycoside, a threonine and a pyridoxine.

Description of the Related Art

Influenza (the flu) is a contagious respiratory illness caused by influenza viruses. It can cause mild to severe illness, and at times can lead to death. According to the CDC, various subtypes of the influenza virus circulate worldwide. It is estimated there are about 306 known human influenza types, subtypes and strains and about 62 known non-polio enteroviruses which cause flu-like illness in humans. Types A and B influenza virus are responsible for seasonal flu epidemics each year usually striking in December through April. Non-polio enteroviruses are second only to the "common cold" viruses as the most common viral infectious agents in humans. Enteroviruses are most likely to occur in June through November. To reduce the likelihood of contracting the A or B influenza virus, one can get a flu vaccine to provide a measure of protection during flu season.

The best way to prevent the flu is by getting a flu vaccination each year. However, the vaccination works only for prophylaxis of certain strains of influenza. In fact, one key disadvantage of vaccines is that they are strain specific. Once the patient is infected, other options must be considered.

In the United States there are two classes of drugs approved by the FDA for treating or preventing influenza virus infection: the M2 ion channel blockers and the neuraminidase inhibitors (NAIs). The M2 channel blockers (adamantanes) such as amantadine and rimantadine are effective against influenza A viruses, but not influenza B viruses since they lack the M2 protein. Use of the M2 blockers is associated with emergence of drug resistant mutations of the M2 protein in human influenza A viruses of H3N2 and H1N1 subtypes, and resistance has been detected in A/H5N1 viruses. Therefore, the CDC has not recommended their use since 2005 and now recommends the exclusive use of NAIs; except in possible cases of NAI resistant strains. Viral neuraminidase may facilitate access of virus to cell surfaces and aid the release of newly formed virus particles from infected cells, to allow viral infection of other cells.

If a patient contracts an A or B influenza virus strain, NAIs such as Relenza® (zanamivir) and Tamiflu® (oseltamivir) are available only by prescription and are meant to be started during the first 48 hours after onset of symptoms. These NAI drugs have been shown to reduce the duration of a typical seven day illness by about one day. For treatment of 2009 H1N1 virus infection, the CDC currently recommends use of either oseltamivir (Tamiflu®) or zanamivir (Relenza®) (http://www.cdc.gov/h1n1flu/recommendations.htm). After symptoms appear both influenza and non-polio enteroviruses are also treated symptomatically to ease discomfort.

Tamiflu® (oseltamivir phosphate, Roche) is an antiviral prescription drug in the form of oral capsules or oral suspensions approved for the treatment and prophylaxis of influenza. Oseltamivir phosphate is an ethyl ester prodrug requiring ester hydrolysis for conversion to the active form, oseltamivir carboxylate. Oseltamivir carboxylate is an inhibitor of influenza virus neuraminidase affecting release of virus particles. Influenza A virus isolates with reduced susceptibility to oseltamivir carboxylate have been recovered by serial passage of virus in cell culture in the presence of increasing concentrations of oseltamivir carboxylate. In clinical studies of the treatment of naturally acquired infection with influenza virus, 1.3% of post-treatment isolates in adults and adolescents and 8.6% of post-treatment isolates in children aged 1 to 12 years showed emergence of influenza variants with decreased neuraminidase susceptibility in cell culture to oseltamivir carboxylate. Cross-resistance between certain zanamivir-resistant influenza mutants and oseltamivir-resistant influenza mutants has been observed in cell culture. During the 2007-2008 influenza season, oseltamivir resistance among influenza A (H1N1) viruses increased significantly for the first time worldwide (Dharan et al., Infections with Oseltamivir-resistant influenza A(H1N1) virus in the United States, JAMA 301 (10), 1034-1041 (2009)). Influenza B viruses with reduced sensitivity to neuraminidase inhibitors do not arise as frequently as resistant influenza A viruses. However, they appear to be transmitted within communities and families (Hatakeyama et al., Emergence of influenza B viruses with reduced sensitivity to neuraminidase inhibitors. JAMA, 297:13:1492-1493 (2007)).

Side effects can also occur with treatment with NAIs. For example, Roche and the FDA informed healthcare professionals in March 2008 of neuropsychiatric events associated with the use of Tamiflu®, in patients with influenza. The label was revised to state that influenza can be associated with a variety of neurologic and behavioral symptoms which can include events such as hallucinations, delirium, and abnormal behavior, in some cases resulting in fatal outcomes. These events were reported primarily among pediatric patients and often had an abrupt onset and rapid resolution. Because these events were reported voluntarily during clinical practice, estimates of frequency cannot be made but they appear to be uncommon based on Tamiflu® usage data. Nevertheless, due to emerging drug resistant influenza strains and possible side effects of Tamiflu®, alternative antiviral therapy is of interest.

Relenza® (zanamivir, GlaxoSmithKline) is an antiviral prescription drug in the form of an inhalation powder approved for the treatment and prophylaxis of influenza. Zanamivir acts as an inhibitor of the influenza virus surface enzyme neuraminidase. Viral neuraminidase may facilitate access of virus to cell surfaces and aid the release of newly formed virus particles from infected cells, to allow viral infection of other cells. Influenza viruses with reduced susceptibility to zanamivir have been recovered in vitro by passage of the virus in the presence of increasing concentrations of the drug. Zanamivir resistant influenza viruses with a novel neuraminidase mutation have been recently identified (Hurt et al., J. Virology, 83(20):10366-10373 (October 2009)).

There remains great uncertainty about the usefulness of these drugs in a pandemic because access may be limited and drug resistance may develop. Clearly, alternative methods of treatment and prophylaxis of viral infection are desired to help limit development of drug-resistance to known antiviral pharmaceuticals.

Several antiviral supplement formulations comprising various vitamins and minerals are known and some are available commercially. Many of these formulations are made up of dietary supplements as defined under the Federal Food, Drug and Cosmetic Act, Chapter II Section 201, [21 U.S.C. § 321], paragraph ff, and thus may be classified as dietary supplements rather than drugs.

U.S. Pat. No. 5,626,883, Paul, discloses ascorbic acid compositions providing enhanced human immune system activity. The Paul compositions include a water soluble ascorbate, a fat soluble ascorbyl ester, and at least one ascorbic acid metabolite selected from basic amino acids, metabolic by-products of ascorbic acid breakdown, flavonoids, sulfur containing amino acids, tetrasodium pyrophosphate, and glutathione.

WO 2007/106675, Rath et al. and U.S. Pat. No. 2007/0212426, Rath et al. each disclose a composition and method of retarding viral activity and reducing viral replication comprising administering a composition comprising polyphenols, an ascorbic compound, lysine and proline.

U.S. Pat. No. 7,041,699, Netke et al. disclose nutrient pharmaceutical formulations comprising polyphenols and use in treatment of cancer. Netke et al. disclose formulations comprising an ascorbic compound, the amino acids lysine, proline and N-acetylcysteine, and at least one polyphenol.

WO 92/15315, Wilkinson, discloses a method for treating a herpes infection which comprises administering a composition comprising lysine, vitamin C and hesperidin.

U.S. Pat. No. 5,650,418, Rath and Pauling, disclose a pharmaceutical composition consisting essentially of an ascorbate compound and a lysine in the presence of a pharmaceutical carrier. Rath and Pauling also disclose a method of treating cardiovascular disease by administering a composition comprising an ascorbate, nicotinic acid, a lysine, and a pharmaceutical carrier.

A novel antiviral formulation comprising a lysine, an ascorbic compound, a flavonoid glycoside, a threonine and a pyridoxine has been found to be surprisingly effective at inhibition of influenza A and neuraminidase expression in vitro when compared to other dietary supplement formulations as well as oseltamivir.

BRIEF SUMMARY OF THE DISCLOSURE

In one embodiment, the disclosure provides an oral antiviral supplement composition comprising a lysine, an ascorbic compound, a flavonoid glycoside, a threonine, and a pyridoxine. In one aspect, the lysine is selected from L-lysine, L-lysine monohydrochloride, L-lysine dihydrochioride, L-lysine succinate, L-lysine glutamate, and L-lysine orotate. In another aspect, the ascorbic compound is selected from one or more of ascorbic acid, calcium ascorbate, magnesium ascorbate, potassium ascorbate, sodium ascorbate, manganese ascorbate, zinc ascorbate, iron ascorbate, copper ascorbate, boron ascorbate, molybdenum ascorbate, chromium ascorbate, ascorbyl palmitate, ascorbyl arachidonate, ascorbyl stearate, ascorbyl linoleate, ascorbyl linoleneate, and ascorbyl oleate. In a further aspect, the flavonoid glycoside is selected from one or more of hesperidin, rutin, naringin, and quercitrin. In one specific aspect, the flavonoid glycoside is about a 1:1 mixture by weight of hesperidin and rutin. In one aspect, the pyridoxine is pyridoxine hydrochloride. In another aspect, the composition further comprises taurine.

In one aspect, the composition is in a powder, capsule, lozenge, troche, tablet, liquid, or caplet form. In one aspect, the composition comprises L-lysine monohydrochloride, ascorbic acid, hesperidin, rutin, pyridoxine hydrochloride, threonine, and taurine. In one aspect, the composition further comprises calcium ascorbate, niacinamide ascorbate, and ascorbyl palmitate.

In one specific aspect, a single dose of the composition comprises from about 2 g to about 3.5 g L-lysine monohydrochloride; from about 0.1 g to about 1.5 g ascorbic acid; from about 0.2 g to about 0.8 g hesperidin; from about 0.1 g to about 0.5 g rutin; from about 0.04 g to about 0.08 g pyridoxine hydrochloride; from about 0.01 g to about 0.08 g threonine; and from about 0.02 g to about 0.4 g taurine. In another specific aspect, the composition further comprises from about 0.5 g to about 0.75 g calcium ascorbate; from about 0.1 g to about 0.5 g niacinamide ascorbate; and from about 0.01 g to about 0.1 g ascorbyl palmitate. In another specific aspect, a single dose of the composition comprises about 3 g L-lysine monohydrochloride; from about 0.2 g to about 1.0 g ascorbic acid; about 0.3 g hesperidin; about 0.3 g rutin; about 0.05 g pyridoxine hydrochloride; about 0.05 g threonine; and from about 0.02 g to about 0.3 g taurine. In a further specific aspect, a single dose of the composition further comprises about 0.6 g calcium ascorbate; 0.3 g niacinamide ascorbate, and about 0.05 g ascorbyl palmitate.

In another embodiment, the disclosure provides a method of reducing viral replication in a cell comprising treating a virus-infected cell with an effective amount of a composition comprising a lysine, an ascorbic compound, a flavonoid glycoside, a threonine and a pyridoxine. In one aspect, the method utilizes a composition wherein the lysine is selected from L-lysine, L-lysine monohydrochloride, L-lysine dihydrochloride, L-lysine succinate, L-lysine glutamate, and L-lysine orotate. In another aspect, the method utilizes a composition wherein the ascorbic compound is selected from one or more of ascorbic acid, calcium ascorbate, magnesium ascorbate, potassium ascorbate, sodium ascorbate, manganese ascorbate, zinc ascorbate, iron ascorbate, copper ascorbate, boron ascorbate, molybdenum ascorbate, chromium ascorbate, ascorbyl palmitate, ascorbyl arachidonate, ascorbyl stearate, ascorbyl linoleate, ascorbyl linoleneate, and ascorbyl oleate. In another aspect, the method utilizes a composition wherein the flavonoid glycoside is selected from one or more of hesperidin, rutin, naringin, and quercitrin. In another aspect, the method utilizes a composition wherein the pyridoxine is pyridoxine hydrochloride. In another aspect, the method utilizes a composition further comprising taurine.

In another specific aspect, the disclosure provides a method of reducing viral replication in a cell comprising treating a virus-infected cell with an effective amount of a composition comprising L-lysine monohydrochloride, ascorbic acid, calcium ascorbate, niacinamide ascorbate, ascorbyl palmitate, hesperidin, rutin, pyridoxine hydrochloride, threonine, and taurine.

In a further embodiment, the disclosure provides a method for the treatment or prophylaxis of a viral infection in a subject in need thereof comprising administering to the subject a therapeutically effective amount of a composition comprising a lysine, an ascorbic compound, a flavonoid glycoside, a threonine, and a pyridoxine. In certain aspects, the viral infection is an influenza A, influenza B, influenza C or a non-polio enterovirus infection. In another aspect, the method utilizes a composition wherein the lysine is selected from L-lysine, L-lysine monohydrochloride, L-lysine dihydrochloride, L-lysine succinate, L-lysine glutamate, and L-lysine orotate. In another aspect, the method utilizes a composition wherein the ascorbic compound is selected from one or more of ascorbic acid, calcium ascorbate, magnesium ascorbate, potassium ascorbate, sodium ascorbate, manganese ascorbate, zinc ascorbate, iron ascorbate, copper ascorbate, boron ascorbate, molybdenum ascorbate, chromium ascorbate, ascorbyl palmitate, ascorbyl arachidonate, ascorbyl stearate, ascorbyl linoleate, ascorbyl linoleneate, and ascorbyl oleate. In another aspect, the method utilizes a composition wherein the flavonoid glycoside is selected from one or more of hesperidin, rutin, naringin, and quercitrin. In another aspect, the method utilizes a composition wherein the pyridoxine is pyridoxine hydrochloride. In another aspect, the method utilizes a composition further comprising taurine. In another aspect, the method utilizes a composition comprising L-lysine monohydrochloride, ascorbic acid, calcium ascorbate, niacinamide ascorbate, ascorbyl palmitate, hesperidin, rutin, pyridoxine hydrochloride, threonine, and taurine. In another aspect, the method utilizes a composition that further comprises calcium ascorbate, niacinamide ascorbate, and ascorbyl palmitate.

In one specific aspect, the method for the treatment or prophylaxis of a viral infection in a subject in need thereof comprises administering to the subject a therapeutically effective amount of a composition wherein a single dose comprises from about 2 g to about 3.5 g L-lysine monohydrochloride; from about 0.1 g to about 1.5 g ascorbic acid; from about 0.2 g to about 0.8 g hesperidin; from about 0.1 g to about 0.5 g rutin; from about 0.04 g to about 0.08 g pyridoxine hydrochloride; from about 0.01 g to about 0.08 g threonine; and from about 0.02 g to about 0.4 g taurine. In a further specific aspect, the method utilizes a composition wherein a single dose further comprises from about 0.5 g to about 0.75 g calcium ascorbate; from about 0.1 g to about 0.5 g niacinamide ascorbate; and from about 0.01 g to about 0.1 g ascorbyl palmitate. In another specific aspect, the method utilizes a composition wherein a single dose comprises about 3 g L-lysine monohydrochloride; from about 0.2 g to about 1.0 g ascorbic acid; about 0.3 g hesperidin; about 0.3 g rutin; about 0.05 g pyridoxine hydrochloride; about 0.05 g threonine; and from about 0.02 g to about 0.3 g taurine. In a further specific aspect, the method utilizes a composition wherein a single dose further comprises about 0.6 g calcium ascorbate; 0.3 g niacinamide ascorbate, and about 0.05 g ascorbyl palmitate.

Figure 1:
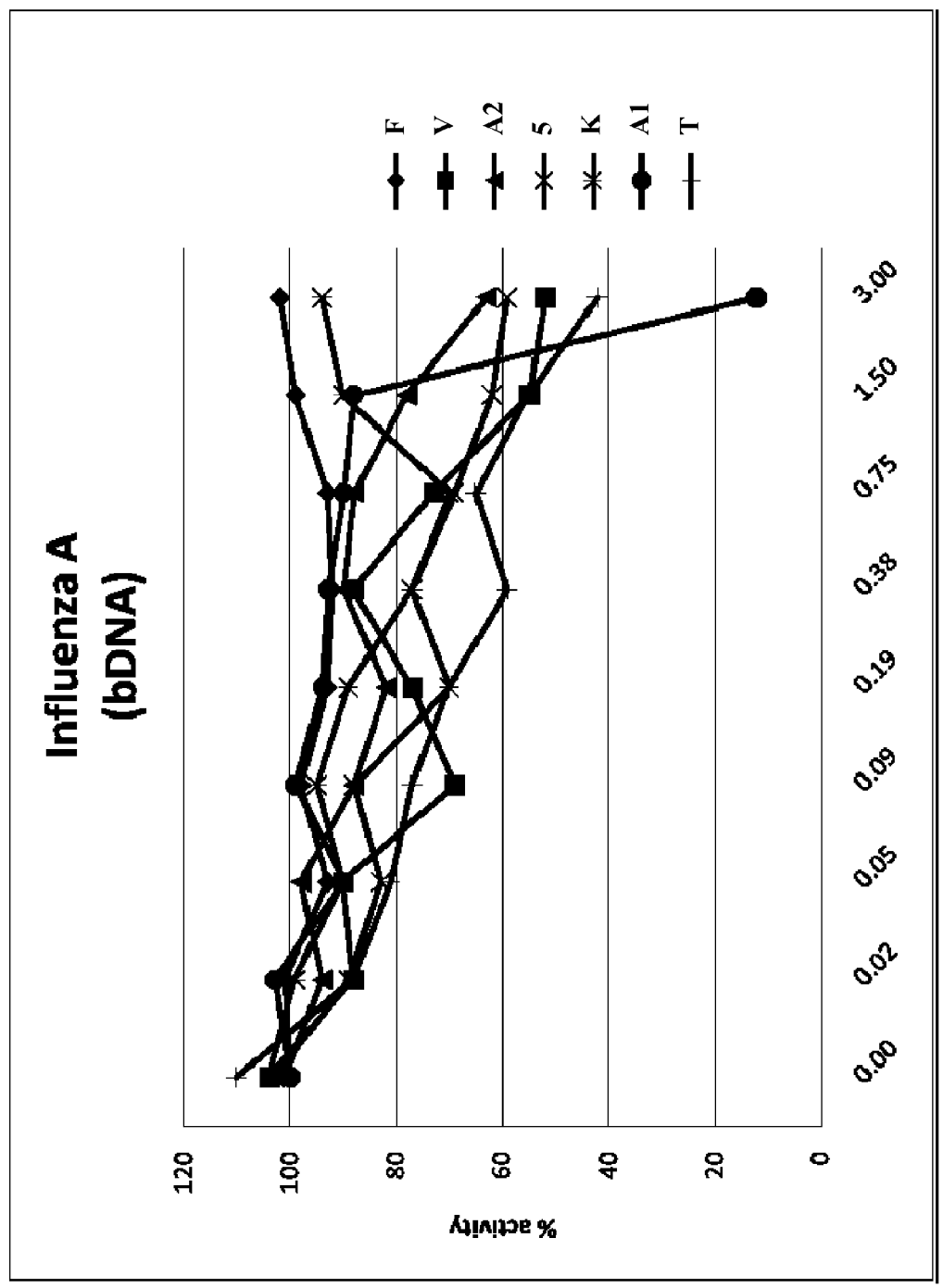
FIG. 1 shows a concentration (uM)/response graph for in vitro inhibition of influenza A infection of Vero cells when treated with various formulations in a branched chain DNA (bDNA) assay of infected cell supernatants as described in Example 2. The data represents the mean (n=3) for each data point, but error bars have been omitted for clarity.

FIG. 2 shows a concentration (uM)/response graph for in vitro inhibition of influenza A infection of Vero cells when treated with various formulations in a bDNA assay as described in Example 2. The data represents the mean (n=3) for each data point; the error bars represent standard error of the mean (SEM).

FIG. 3 shows inhibition of neuraminidase from influenza A infected Vero cell supernatants in vitro by various formulations in the Amplex Red Neuraminidase assay as described in Example 3. The data represents the mean (n=3) for each data point, but error bars have been omitted for clarity.

FIG. 4 shows inhibition of neuraminidase from influenza A infected Vero cell supernatants in vitro by two formulations in the Amplex Red Neuraminidase assay as described in Example 3. The data represents the mean (n=3) for each data point; the error bars represent standard error of the mean (SEM).

FIG. 5 shows inhibition of matrix metalloproteinase 9 (MMP-9) expression in influenza-A-infected Vero cells by various formulations (uM) as described in Example 4. The data represents the mean (n=3) for each data point, but error bars have been omitted for clarity.

FIG. 6 shows inhibition of matrix metalloproteinase 9 (MMP-9) expression in influenza-A-infected Vero cells by two formulations as described in Example 4. The data represents the mean (n=3) for each data point; the error bars represent standard error of the mean (SEM).

FIG. 7 shows a table (Table 4) of various compositions tested in the Neuraminidase assay.

FIG. 8 shows a graph of neuraminidase activity of human influenza virus infected cells after exposure to oseltamivir carboxylate, Formula V and ten test compositions from Table 4 containing various components of Formula V.

FIG. 9 shows neuraminidase activity of human influenza virus infected cells after exposure to oseltamivir carboxylate, Formula V and either lysine alone (1) or lysine with ascorbic acid/ascorbates (1/2; 9A).

FIG. 10 shows neuraminidase activity of human influenza virus infected cells after exposure to oseltamivir carboxylate, Formula V and either lysine/ascorbates/flavonoid glycosides (1/2/3; 10A) or lysine/ascorbates/pyridoxine (1/2/4; 10B).

FIG. 11 shows neuraminidase activity of human influenza virus infected cells after exposure to oseltamivir carboxylate, Formula V and either lysine/ascorbates/threonine (1/2/5; 11A) or lysine/ascorbates/taurine (1/2/6; 11B).

FIG. 12 shows neuraminidase activity of human influenza virus infected cells after exposure to oseltamivir carboxylate, Formula V and either lysine/ascorbates/pyridoxine HCl/threonine (1/2/4/5; 12A) or lysine/ascorbates/flavonoid glycosides/threonine (1/2/3/5; 12B).

FIG. 13 shows neuraminidase activity of human influenza virus infected cells after exposure to oseltamivir carboxylate, Formula V and either lysine/ascorbates/flavonoid glycosides/pyridoxine HCl/threonine (1/2/3/4/5; 13A) or lysine/ascorbic acid/flavonoid glycosides/pyridoxine HCl/threonine/taurine (1/2/3/4/5/6; 13B).

DETAILED DESCRIPTION

The disclosure provides novel antiviral supplement compositions comprising a lysine, an ascorbic compound, a flavonoid glycoside, a threonine, and a pyridoxine. The disclosure provides compositions in the form of a powder, capsule, tablet, lozenge, troche, liquid, or caplet. A specific embodiment discloses a powder comprising lysine, ascorbic acid, flavonoid glycosides, pyridoxine hydrochloride, taurine, and threonine.

The term "patient" or "subject" as used herein refers to an animal, for example a mammal, such as a human, who is the object of treatment. The subject, or patient, may be either male or female.

The term "about" as used herein refers to a numeric range that is +1-10% of the given quantity. For example, the term "about 50%" refers to 45% to 55%, and "about 100 mg" refers to 90 mg to 110 mg.

The term "virus" used herein refers to any of a large group of submicroscopic agents that consist of a segment of DNA or RNA surrounded by a coat of protein. Influenza viruses and enteroviruses are RNA viruses. The virus is a parasite that needs a host cell to replicate. Because viruses are unable to replicate without a host cell, they are not considered living organisms in conventional taxonomic systems. They are described as "live" when they are capable of replicating and causing disease. Accordingly, the term "viral activity" refers to any state of being active or any energetic action or movement or liveliness of a virus. Accordingly, the term "viral replication" refers to any process by which genetic materials, a single-celled organism, or a virus reproduces or makes a copy of itself.

The term "Neuraminidase" as used herein refers to a viral neuraminidase protein that acts as a hydrolytic enzyme that removes sialic acid from mucoproteins and is found chiefly in microorganisms of the respiratory and intestinal tracts. Neuraminidase breaks the bonds that hold new virus particles to the outside of an infected cell. Once the enzyme breaks these bonds, this sets free new viruses that can infect other cells and spread infection.

The term "Neuraminidase inhibitor" (NAI) as used herein refers to a drug or formulation that blocks the function of neuraminidase protein and therefore prevents new virus particles from being released, thereby limiting the spread of infection. Specific NAIs include oseltamivir, zanamivir, laninamivir and peramivir.

The term "Vero cells" as used herein refers to the African green monkey kidney cell line which is a suitable system for the primary isolation and cultivation of influenza A viruses. It is also known that Vero cells are suitable for isolation and productive replication of influenza B viruses.

The term "infection" as used herein refers to the presence of a virus in or on a subject, which if replication of the virus was retarded or of the activity of the virus was reduced, would result in a benefit to the subject. Accordingly, the term "infection" refers to the presence of pathogens at any anatomical site of a human or animal.

The term "treating" as used herein refers to the administration of a compound or composition to a subject for therapeutic purposes. The term "administration" includes delivery to a subject by any appropriate method which serves to deliver the drug to the site of the infection. The administration of the drug can be oral, nasal, parental, topical, ophthalmic, or transdermal administration or delivery in the form of solid, semi-solid, lyophilized powder, or liquid dosage forms. The dosage forms include tablets, capsules, troches, powders, solutions, suspensions, suppositories, or the like, preferably in unit dosage forms suitable for simple administration of precise dosages.

The term "antiviral supplement" as used herein includes any composition used specifically for treatment or prophylaxis of viral infections, particularly influenza virus or non-polio enterovirus infections. The compositions of the disclosure can be evaluated in one aspect by various neuraminidase assays. In another aspect, the compositions of the disclosure can be evaluated by retarding the growth and reproduction of viruses in a cell based assay. In another aspect, the compositions of the disclosure can be evaluated by decreasing the duration of a viral infection in a patient. In another aspect, the compositions of the disclosure can be evaluated by decreasing the severity or duration of symptoms of a viral infection in a patient.

As used herein, the term "pharmaceutically acceptable salt" refers to those salts which retain the biological effectiveness and properties of the active ingredient of the biochemical composition, which are not otherwise undesirable. Pharmaceutically acceptable salts include, but are not limited to, salts of sodium, potassium, calcium, magnesium, aluminum and the like.

As used herein, the term "an effective amount" refers to that an amount of a composition of the disclosure that when administered to an individual subject in need thereof, is sufficient to reduce the virus activity and/or growth thereby enhancing the antiviral activity.

As used herein, the term "therapeutically effective amount" refers to an amount of a composition of the disclosure that when administered to a human subject in need thereof, is sufficient to effect treatment or prophylaxis for influenza virus infection, or non-polio enterovirus infection. The amount that is therapeutically effective will depend upon the patient's size and gender, the stage and severity of the infection and the result sought. For a given patient and condition, a therapeutically effective amount can be determined by methods known to those of skill in the art. For example, in reference to the treatment of a influenza virus infection using the compositions of the present invention, a therapeutically effective amount refers to that amount of the composition which has the effect of (1) reducing the shedding of the virus, (2) reducing the duration of the infection, (3) reducing infectivity and/or, (4) reducing the severity (or, preferably, eliminating) one or more other symptoms associated with the infection such as, for example, fever, headache, fatigue, dry cough, sore throat, muscle aches, conjunctivitis, runny and/or stuffy nose. Such an effective dose will generally depend on the factors described above. A prophylactically effective dose is one that reduces the likelihood of contacting an influenza virus infection, or non-polio enterovirus infection. A prophylactically effective dose is from about 20% to about 100%, preferably from about 40% to about 60%, of a therapeutically effective dose.

In one aspect, the administration is oral administration. Generally, a therapeutically effective dose is not less than about 10% and not more than about 200% of the amounts of individual ingredients listed in Table 1. In certain aspects, a therapeutically effective dose for treatment of a viral infection is from about 50% to about 150%, or from about 80% to about 120%, or about 100% identical with the list of components in Table 1. In another aspect, a therapeutically effective dose for treatment of a viral infection in a subject in need thereof is administered every 4 to 6 waking hours, or from about two to six times per day. In a further aspect, a therapeutically effective dose for prophylaxis of a viral infection in a subject in need thereof is administered every 8 to 12 waking hours, or from about one to three times per day.

The term, "pharmaceutically acceptable carrier" as used herein means a pharmaceutically-acceptable material, composition or vehicle, such as a liquid or solid filler, diluent, excipient, solvent or encapsulating material, involved in carrying or transporting the compositions of the invention from one organ, or portion of the body, to another organ, or portion of the body without affecting its biological effect. Each carrier should be "acceptable" in the sense of being compatible with the other ingredients of the composition and not injurious to the subject.

Symptoms of influenza can include fever, headache, fatigue, dry cough, sore throat, muscle aches, runny and/or stuffy nose. Gastrointestinal symptoms such as nausea, vomiting and diarrhea can also occur, but are more common in children than adults.

Symptoms of non-polio enteroviruses include fever, muscle aches, upper respiratory symptoms, tiredness, and flu-like illness with rash.

Viruses spread from person to person primarily through coughing or sneezing. People may also become infected by contact with contaminated surfaces or objects, then by touching their mouth or nose. Most healthy adults may be able to infect others beginning about one day before symptoms develop and up to about five days after becoming ill.

Influenza viruses are dynamic and are continuously evolving. Influenza viruses can change in two different ways: antigenic drift and antigenic shift. Influenza viruses are constantly changing by antigenic drift, but antigenic shift occurs only occasionally. Influenza type A viruses undergo both kinds of changes; influenza type B viruses change only by the more gradual process of antigenic drift. Antigenic drift refers to small, gradual changes that occur through point mutations in the two genes that contain the genetic material to produce the main surface proteins, hemagglutinin, and neuraminidase. These point mutations occur unpredictably and result in minor changes to these surface proteins. Antigenic drift produces new virus strains that may not be recognized by antibodies to earlier influenza strains.

Humans can be infected with influenza types A, B, and C viruses. Influenza A, B, and C are responsible for producing 306 human influenza viruses. Subtypes of influenza A that are currently circulating among people worldwide include H1N1, H1N2, and H3N2 viruses.

Based on global experience to date, 2009 H1N1 influenza viruses likely will be the most common influenza viruses among those circulating in the coming flu season, particularly those causing influenza among younger age groups. (CDC "Updated Interim Recommendations for the Use of Antiviral Medications in the Treatment and Prevention of Influenza for the 2009-2010 Season, Sep. 22, 2009, http://www.cdc.gov/hlnlflu/recommendations.htm)

Wild birds are a natural host for known subtypes of influenza A viruses. Typically, wild birds do not become sick when they are infected with avian influenza A viruses. However, domestic poultry can become very sick and die from avian influenza.

Influenza type A viruses are divided into subtypes and named on the basis of two proteins on the surface of the virus: hemagglutinin (HA) and neuraminidase (NA). There are 16 known HA subtypes and 9 known NA subtypes. Many different combinations of HA and NA proteins are possible. Only some influenza A subtypes (i.e., H1N1 "Spanish Flu" or "Swine Flu", H1N2, and H3N2 "Hong Kong Flu") are currently in general circulation among people. Only influenza A viruses infect birds, and all known subtypes of influenza A viruses can infect birds. However, there are substantial genetic differences between the influenza A subtypes that typically infect birds and those that infect both people and birds. Three prominent subtypes of the avian influenza A viruses are known to infect both birds and people.

Influenza A H7 includes several subtypes. H7 infection in humans is rare but can occur among persons who have direct contact with infected birds. Symptoms may include conjunctivitis and/or upper respiratory symptoms. H7 viruses have been associated with both LPAI (e.g., H7N2, H7N7) and HPAI (e.g., H7N3, H7N7), and have caused mild to severe and fatal illness in humans.

Influenza A H5 includes several known subtypes including the highly pathogenic H5N1. A bird adapted strain of H5N1 is called HPAI H5N1 (highly pathogenic avian influenza virus of type A of subtype H5N1), commonly known as "avian influenza" or "bird flu". HPAI H5N1 viruses are currently circulating in Asia and Europe and can cause severe illness or death. HPAI H5N1 is considered a potential agricultural bioweapon. Low pathogenic avian influenza H5N1 (LPAI H5N1), also called "North American" H5N1, occurs in wild birds and causes minor illness or no noticeable signs in birds and is not known to affect humans, but it is possible to be transmitted to poultry and possibly mutate to a highly pathogenic strain.

Low pathogenic avian influenza A (H9N2) was confirmed in 1999. Several potential subtypes of H9 are known; however, influenza A H9 has rarely been reported to infect humans. This subtype has been documented only in a low pathogenic form.

Influenza B viruses are usually found only in humans. Unlike influenza A viruses, these viruses are not classified according to subtype. Influenza B viruses can cause morbidity and mortality among humans, but in general are associated with less severe epidemics than influenza A viruses. Although influenza type B viruses can cause human epidemics, they have not caused pandemics.

Influenza type C viruses cause mild illness in humans and do not cause epidemics or pandemics. These viruses are not classified according to subtype.

Influenza B viruses and subtypes of influenza A virus are further characterized into strains. There are many different strains of influenza B viruses and of influenza A subtypes. New strains of influenza viruses appear and replace older strains. This process occurs through antigenic drift. When a new strain of human influenza virus emerges, antibody protection that may have been developed after infection or vaccination with an older strain may not provide protection against the new strain.

Evidence that influenza can be more severe in pregnant women is available from observations during previous pandemics and from studies among pregnant women who had seasonal influenza. An excess of influenza-associated deaths among pregnant women were reported during the pandemics of 1918-1919 and 1957-1958. Adverse pregnancy outcomes have been reported following previous influenza pandemics, with increased rates of spontaneous abortion and preterm birth reported, especially among women with pneumonia (http://www.cdc.gov/H1N1flu/clinician_pregnant.htm, Jun. 30, 2009). Pregnant women and women up to 2 weeks postpartum are considered to be at higher risk of complications from influenza infection.

Oseltamivir, zanamivir, amantidine and rimantidine are "Pregnancy Category C" medications indicating no studies have been performed to assess the safety of these drugs in pregnant women. Limited cases of amantadine use for severe influenza illness during the third trimester have been reported. However, both amantadine and rimantadine have been demonstrated in animal studies to be teratogenic and embryotoxic when administered at substantially high doses. Because of the unknown effects of influenza antiviral drugs on pregnant women and their fetuses, these four drugs should be used during pregnancy only if the potential benefit justifies the potential risk to the embryo or fetus (Prevention & Control of Influenza—Recommendations of the Advisory Committee on Immunization Practices (ACIP) 2004. MMWR 2004 May 28; 53(RR06); 1-40.) None-the-less, the CDC states that the available risk-benefit data indicate that pregnant women with suspected or confirmed influenza should receive prompt antiviral treatment.

Figure 5:
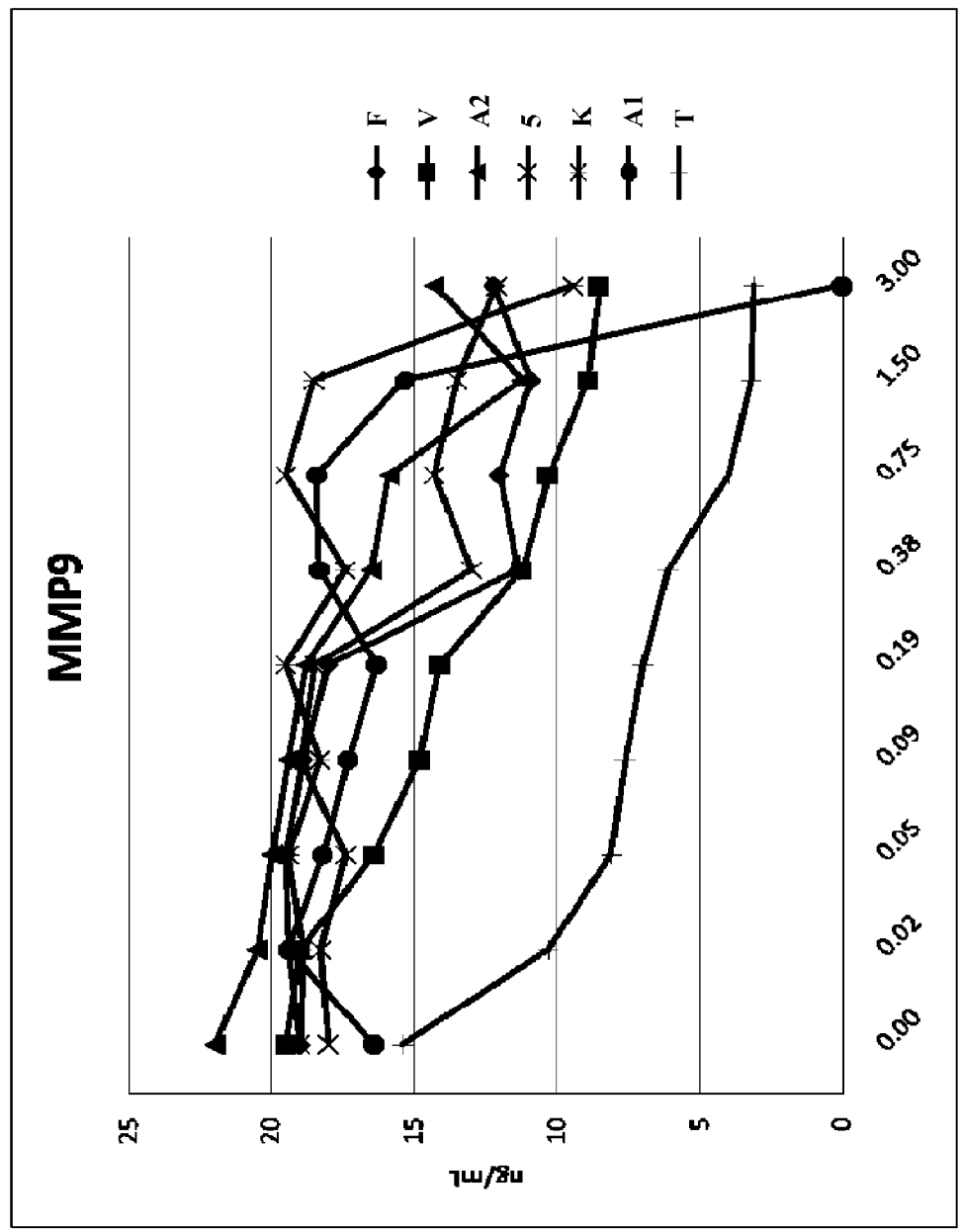

Matrix metalloproteinases (MMPs) are protein enzymes involved in the breakdown of extracellular matrix in normal physiological processes such as tissue remodeling, reproduction and embryonic development. MMPs are important enzymes in tissue remodeling, a key event for the development of fetal membranes and placenta and establishing the feto-maternal interface during early pregnancy. Most MMPs are secreted as inactive proteins which are activated when cleaved by extracellular proteinases. MMP-2 (72 kDa type IV collagenase) and MMP-9 (gelatinase B, 92 kD type IV collagenase) are key effectors of extracellular matrix remodeling. Studies indicate MMP-2 and MMP-9 are present in first trimester extra-embryonic coelomic fluid and in the amniotic fluid at all gestations. The predominant MMP activated protein is the latent form of MMP-2 which is found present in increasing concentrations in amniotic fluid from the first to the second trimester (Riley et al., Secretion of matrix metalloproteinase-2, matrix metalloproteinase-9 and tissue inhibitor of metalloproteinases into the intrauterine compartments during early pregnancy. Molecul. Human Reprod. 5(4): 676-381 (1999)). Tamiflu® inhibits expression of MMP-9, as shown in FIG. 5, which may contribute to increased risk in pregnancy.

Figure 6:
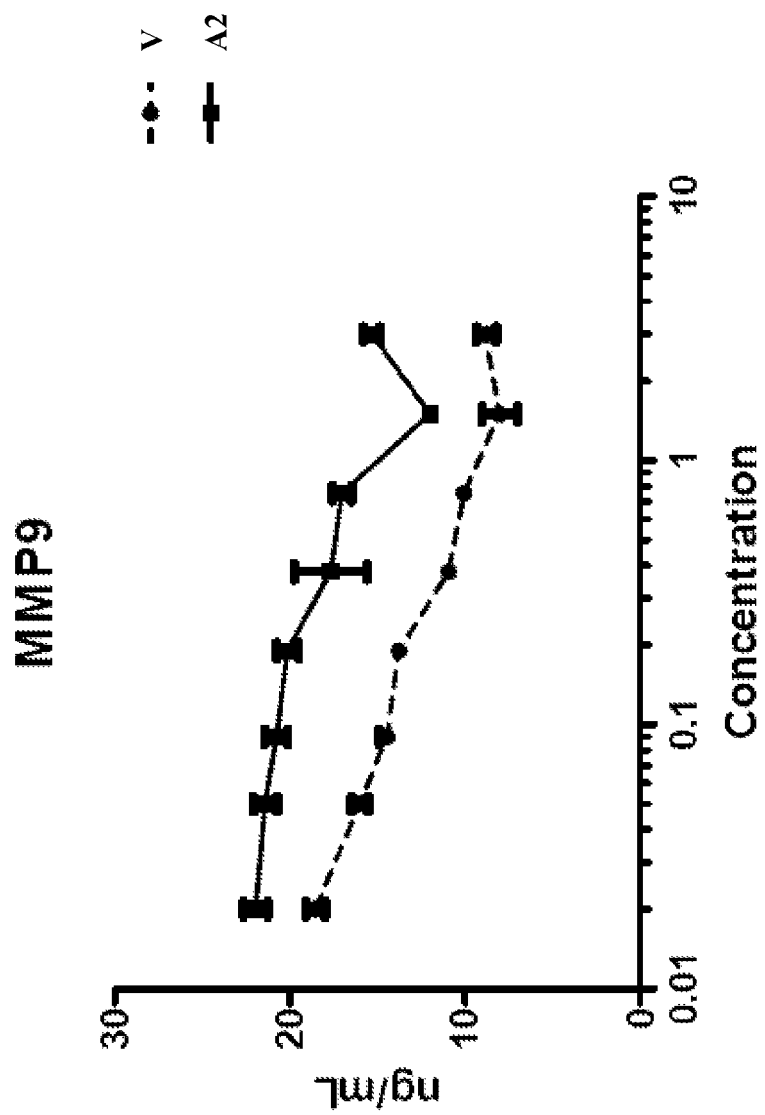

In one embodiment, compositions of the disclosure only weakly inhibit the expression of MMP-9, which may result in greater safety in the treatment of influenza in pregnant women. Data is shown in FIGS. 5 and 6. In another embodiment, compositions of the disclosure have been demonstrated to show no significant inhibition of expression of MMP-2, as discussed in Example 5, which may result in greater safety in the treatment of influenza in pregnant women.

Enteroviruses are small viruses that are made of ribonucleic acid (RNA) and protein. This group includes the polioviruses, coxsackieviruses, echoviruses, and other enteroviruses. There are 62 non-polio enteroviruses that can cause disease in humans: 23 Coxsackie A viruses, 6 Coxsackie B viruses and 28 echoviruses and 5 other enteroviruses.

Non-polio enteroviruses are very common and second only to the "common cold" virus, called the rhinovirus, as the most common viral infectious agent in humans. Everyone without immunity to a specific enterovirus is at risk of infection. Enterovirus outbreaks commonly occur during the summer through fall.

The present disclosure was developed based upon the recognition that a combination of the supplements L-lysine and ascorbic acid is somewhat effective in reducing viral replication and reducing viral infection. In one embodiment, the disclosure provides an antiviral supplement composition which surprisingly further reduces viral replication and inhibits viral infection. Specifically, the disclosure provides an antiviral supplement composition comprising a lysine, an ascorbic compound, a flavonoid glycoside, a pyridoxine, taurine and threonine which has been found to have significantly improved antiviral properties.

In another embodiment, the disclosure provides a method of reducing the severity and duration of symptoms of an influenza infection in a human by administering the composition. In this embodiment, the compositions are taken at the first signs of flu-like illness. In one aspect, the composition is administered every six waking hours with water until symptoms are resolved. In another aspect, the compositions are administered about every four hours after first symptoms appear. In another aspect, the composition is administered twice a day until symptoms are resolved.

In another embodiment, the composition of the present disclosure reduces influenza viral infection of cells. In one aspect, the compositions act as neuraminidase inhibitors. In another aspect, compositions of the present disclosure weakly inhibit MMP-9 expression in vitro.

It is known that vitamin C (ascorbic acid) is necessary for general good health in humans. Humans lack the biochemical mechanisms to synthesize vitamin C, so it must be supplied in the diet in the form of food or supplement. Englard, S. and Steifter, S. "The Biochemical functions of Ascorbic Acid," Ann. Rev. Nutr. 1986. Except where inborn errors of metabolism such as cystinuria, oxalosis, and hyperuricemia are present, it is known that vitamin C can be taken in megadoses without toxic side effects. See Stanbury, J. B., Wyngaarden, J. B., Fredrickson, D. S., 1972, The metabolic basis of inherited disease. 3rd ed. McGraw Hill.

Vitamin C supports the function of the human immune system. Vitamin C is thought to stimulate the human immune system by enhancing interferon synthesis and lymphocyte activity, particularly the class of lymphocyte referred to as natural killer (NK) cells. Sigel, B. V. & Morton, J. I. "Vitamin C and Immunity: Natural Killer (NK) cell factor" Int. J. Vitamin & Nutrition Res. 1983, 53:179-183; Lovzova, E., Savary, C. A., & Heberman, R. B. "Induction of NK cells activity against fresh human leukemia in culture with interlukin 2" J. Immunology 1987, 138:2718-2727. Natural killer cells are lymphocytes that spontaneously kill tumor or virus-infected cells. Decreased numbers of circulating NK cells have been linked to the development and progression of various immunodeficiencies, viral infections, AIDS, and cancer. Vitamin C is also believed to provide further benefits by acting as an antioxidant aiding the immune system by reducing the amount of free radical damage that can occur as a result of normal body metabolism as well as from exogenous sources.

Studies have shown that vitamin C supplementation (e.g., 500 mg/day) increases plasma concentrations of glutathione. Johnston et al. "Vitamin C Elevates Red Blood Cell Glutathione in Healthy Adults" Am. J. Clin. Nutr. 1993, 58:103-105. Certain data suggest that the thiol antioxidant glutathione (GSH) has an anti-influenza activity in vitro and in vivo. Oxidative stress or other conditions that deplete GSH in the epithelium of the oral, nasal, and upper airway may, therefore, enhance susceptibility to influenza infection.

It is known that infection by RNA virus induces oxidative stress in host cells. Accumulating evidence suggests that cellular redox status plays an important role in regulating viral replication and infectivity. Certain data suggest that the thiol antioxidant GSH has an anti-influenza activity in vitro and in vivo. Specifically, experiments were performed to determine whether the thiol antioxidant glutathione (GSH) blocked influenza viral infection in cultures of Madin-Darby canine kidney cells or human small airway epithelial cells. Protection against production of active virus particles was observed at a low (0.05-0.1) multiplicity of infection (MOI). Cai et al. 2003, Inhibition of influenza infection by glutathione. Free Rad. Biol. And Med. 34 (7): 928-936. It was also found that GSH inhibited expression of viral matrix protein and inhibited virally induced caspase activation and Fas upregulation. Together, the data suggest that the thiol antioxidant glutathione (GSH) has an anti-influenza activity in vitro and in vivo. Oxidative stress or other conditions that deplete GSH in the epithelium of the oral, nasal, and upper airway may, therefore, enhance susceptibility to influenza infection.

In one embodiment, the compositions of the present disclosure comprise vitamin C as one or more forms of ascorbic acid, ascorbyl ester or ascorbate salt; together termed ascorbic compounds. In one aspect, the one or more ascorbic compounds are selected from any biologically acceptable form of an ascorbic acid, ascorbyl ester or ascorbate including either or both water-soluble and fat-soluble forms. The water soluble form of ascorbic acid can be selected from the group consisting of ascorbic acid, a biologically acceptable mono or divalent metal ion salt of ascorbic acid and niacinamide ascorbate, and mixtures thereof. Suitable metal ion salts of ascorbic acid are those selected from the group consisting of calcium ascorbate; magnesium ascorbate; potassium ascorbate; and sodium ascorbate, either alone or some mixture thereof. Other water soluble forms can include manganese ascorbate; zinc ascorbate; iron ascorbate; copper ascorbate; boron ascorbate; molybdenum ascorbate; and chromium ascorbate. The fat soluble ascorbyl esters preferably comprise fatty acid esters of saturated or unsaturated carboxylic acids with ascorbyl palmitate being one preferred form. Other fat soluble esters of ascorbic acid which are preferred include: ascorbyl palmitate; ascorbyl arachidonate; ascorbyl stearate; ascorbyl linoleate; ascorbyl linoleneate; and ascorbyl oleate.

In one aspect, the composition comprises from about 15% to about 35% by weight, preferably about 20% to about 30% by weight combined of one or more ascorbic compounds, or equivalent. In a specific aspect, the composition comprises about 25% by weight of combined ascorbic acid, calcium ascorbate, niacinamide ascorbate, and ascorbyl palmitate. In another aspect, the composition comprises about 0.5 to about 2.0 g, preferably about 0.5 g to about 1.5 g combined weight of one or more ascorbic compounds per dose. In one aspect, certain compositions comprise m about 0.1 g to about 1.5 g ascorbic acid per dose. In another aspect, certain compositions of the disclosure comprise from about 0.5 g to about 0.75 g calcium ascorbate per dose. In a further aspect, certain compositions of the disclosure comprise from about 0.1 g to about 0.5 g niacinamide ascorbate per dose. In another aspect, certain compositions of the disclosure comprise from about 0.01 g to about 0.1 g ascorbyl palmitate per dose.

Lysine is one of the essential amino acids found in proteins. It is needed for proper growth in infants and for maintenance of nitrogen balance in adults. L-lysine is metabolized in mammals to give acetyl-CoA by an initial transamination with alpha-ketoglutarate. Lysine is essential for protein synthesis in the body. L-lysine plays a role in calcium absorption, building muscle protein, recovery from injury, and the body's production of hormones, enzymes and antibodies. L-lysine is known to be used to treat mouth and genital lesions caused by herpes simplex virus as well as shingles caused by herpes zoster viruses. Taking lysine supplements can speed recovery time and reduce the chance of recurrent breakouts of the herpes virus infection. General lysine doses for the treatment of symptoms of herpes virus infection include oral divided doses of about 3 g to about 9 g per day. Lysine supplements are considered generally safe and non-toxic. About 0.5 g to about to 1.5 g per day lysine is suggested to prevent recurrences of outbreak. Griffith et al. Success of L-lysine therapy in frequently recurrent herpes simplex infection. Treatment and prophylaxis. *Dermatologica*. 1987; 175(4):183-190. Proteins of the herpes simplex virus are rich in L-arginine and tissue culture studies have shown that when the ratio of L-lysine to L-arginine is high, viral replication and cytopathogenicity of the herpes simplex virus have been found to be inhibited.

In one embodiment, the compositions of the present disclosure comprise lysine. The term lysine refers to any pharmaceutically acceptable form including a salt of L-lysine which includes lysine hydrochloride, lysine dihydrochloride, lysine succinate, lysine glutamate, lysine orotate as well as L-lysine. Other acceptable forms of lysine include lysine derivatives such as lysine acetate. In one aspect, the composition comprises from about 40% to about 80% by weight, preferably about 50% to about 70% by weight of L-lysine hydrochloride, or equivalent. In a specific aspect, the composition comprises about 60% by weight of L-lysine hydrochloride. In one aspect, the compositions of the disclosure comprise a single dose range of from about 1,000 mg to about 5,000 mg, preferably about 2,000 to about 3,500 mg.

Flavonoids are a large family of compounds synthesized by plants that have a common chemical structure. Flavonoids are further divided into subclasses based upon chemical structure. Flavonoids are found in fruits and vegetables in the diet. Flavonoids connected to one or more sugar molecules are known as flavonoid glycosides, while those that are not connected to a sugar molecule are called aglycones. With the exception of flavanols (catechins and proanthocyanidins), flavonoids occur in plants and most foods as glycosides. Even after cooking, most flavonoid glycosides reach the small intestine intact. Only flavonoid aglycones and flavonoid glucosides (bound to glucose) are absorbed in the small intestine, where they are rapidly metabolized to form methylated, glucuronidated, or sulfated metabolites. The ability of flavonoids to chelate (bind) metal ions appears to contribute to their antioxidant activity in vitro. Although it was initially hypothesized that the biological effects of flavonoids would be related to their antioxidant activity, available evidence from cell culture experiments suggests that many of the biological effects of flavonoids are related to their ability to modulate cell-signaling pathways (Williams et al., Flavonoids: antioxidants or signalling molecules? Free Radic. Biol. Med.; 36(7):838-849 (2004)).

In one aspect, the compositions of the present disclosure comprise one or more flavonoid glycosides. The flavonoid glycosides may include any flavonoid which is glycosylated. In a specific aspect, the compositions comprise one or more flavonoid glycosides selected from hesperidin, rutin, naringin, and quercitrin. In one specific aspect, the compositions comprise hesperidin and rutin.

In one aspect, the composition comprises from about 5% to about 20% by weight, preferably about 10% to about 15% by weight combined of one or more flavonoid glycoside, or equivalent. In a specific aspect, the composition comprises about 12% by weight of combined hesperidin complex and/or rutin. In one aspect, the compositions comprise about from about 0.2 g to about 0.8 g hesperidin per single dose. In another aspect, the compositions comprise from about 0.1 to about 0.5 g rutin per dose.

Threonine is an essential amino acid that is a necessary building block for protein. It promotes the growth of the thymus, a small gland that regulates many of the hormones and cells vital to immune defense. Even a moderate reduction in dietary intake of threonine can produce a depression in immune response or antibody production. Lotan. Humoral and cellular immune response in growing rats fed a 10% gluten diet. Isr. J. Med. Sci. 1989 August; 25(8):437-41. Recent research suggests that the effects of threonine relate to a specific requirement by the thymus for this amino acid and its ability to promote cell immune defense functions. Braverman, Threonine: The Immunity Booster, The Healing Nutrients Within, 2003; 13 pp: 201. In one embodiment, the compositions of the present disclosure comprise threonine. The threonine can be selected from L-threonine or any pharmaceutically acceptable salt or derivative.

In a specific aspect, the threonine is L-threonine. In one aspect, the composition comprises from about 0.1% to about 5% by weight, preferably about 0.5% to about 2% by weight of L-threonine, or equivalent. In a specific aspect, the composition comprises about 1% by weight of L-threonine. In one aspect, the compositions of the disclosure comprise from about 0.01 to about 0.08 g threonine per dose.

In one embodiment, the compositions of the present disclosure comprise pyridoxine. Pyridoxine is one form of vitamin B6. Pyridoxine is utilized by the liver to synthesize pyridoxal phosphate (PLP), the active coenzyme form. PLP is a cofactor for the enzyme threonine aldolase which catalyzes the conversion of hydroxy-N-trimethyl-L-lysine to trimethylaminobutyraldehyde; intermediates in the conversion of L-lysine to L-carnitine. Pyridoxine deficiency is known to produce a significant reduction in plasma carnitine levels. Absorption and Utilization of Amino Acids, Vol. II, Mendel Friedman, CRC Press, 1989, ISBN 0849360072, Ch. III, p. 48-49. Pyridoxine is a water soluble B vitamin which serves as a cofactor and is involved in the metabolism of protein, carbohydrates, and the production of insulin and red and white blood cells. Vitamin B6 is essential in numerous biochemical pathways in the immune system. Pyridoxine deficiency leads to impairment of immune responses (Trakatellis et al., 1997, Pyridoxine deficiency: new approaches in immunosuppression and chemotherapy. Postgrad. Med. J. October; 73(864): 617-622 (1997)). Vitamin B6 is usually safe at intakes up to 200 mg per day in adults.

In one embodiment, the compositions of the present disclosure comprise pyridoxine. In one specific aspect, the pyridoxine is pyridoxine hydrochloride. In one aspect, the composition comprises from about 0.1% to about 2% by weight, preferably about 0.5% to about 1.5% by weight of pyridoxine hydrochloride, or equivalent. In a specific aspect, the composition comprises about 1% by weight of pyridoxine hydrochloride. In one aspect, compositions of the disclosure comprise from about 0.04 g to about 0.08 g pyridoxine hydrochloride per dose.

In one embodiment, the compositions of the present disclosure comprise taurine. Taurine, or 2-aminoethanesulfonic acid, is a metabolite of the sulfur-containing amino acid, cysteine. Taurine is one of the few known naturally occurring sulfonic acids. Metabolic actions of taurine include bile acid conjugation, detoxification, membrane stabilization, osmoregulation, and modulation of cellular calcium levels. Taurine is able to cross the blood brain barrier. Taurine acts as an antioxidant and protects against toxicity of various substances (Green et al., Antioxidant role and subcellular location of hypotaurine and taurine in human neutrophils. Biochimica et biophysica acta January 23; 1073(1):91-7 (1991)). Taurine is also known to play a role in the immune system. For example, taurine interacts with hypochlorous acid, produced during the "oxidant burst" of stimulated macrophages, to produce taurine chloramine (TauCl). This compound may have important immunomodulatory properties and may be responsible for properties that have been ascribed earlier to taurine. In vitro studies have shown that an increase in taurine concentration from physiological to superphysiological concentrations has no effect on proinflammatory cytokine production by peripheral blood mononuclear cells; however, Tau-Cl modulates synthesis of pro-inflammatory cytokines, and therefore it may play a role in the initiation and propagation of immune response (Chorazy et al., Taurine chloramine modulates cytokine production by human peripheral blood mononuclear cells. Amino Acids. 23:407-13 (2002)). Tau-Cl inhibits nuclear factor κB activation and the capacity for proinflammatory cytokine production, producing an anti-inflammatory effect (Huxtable R J., Taurine past, present, and future. Adv Exp Med Biol. 403:641-50 (1996)). Although the maximum safe level of dietary taurine has not been established, 0.9 to 1.4 grams per day have been tolerated without documented adverse effects (Braverman, *Taurine: The Seizure Fighter*, The Healing Nutrients Within, Basic Health Publications, Inc., Laguna Beach, Calif., Ch. 8, pp: 132-133 (2003)).

In one embodiment, compositions of the present disclosure optionally comprise a taurine, or pharmacologically acceptable salt or derivative thereof. In one aspect, the composition comprises from about 1% to about 10% by weight, preferably about 2% to about 6% by weight of taurine, or equivalent. In a specific aspect, the composition comprises about 4% by weight of taurine. In one aspect, compositions of the disclosure comprise from about from about 0.02 g to about 0.4 g taurine per dose.

The compositions of the present disclosure are oral compositions. In one embodiment, the oral composition can be in the form of a powder, capsule, tablet, troche, liquid, or caplet. The powder may be utilized in a capsule fill, or sold in a single dose packet meant to mix with a food such as applesauce, or can be an effervescent powder formulation sold in a single dose packet and meant for suspension in a liquid. In one aspect, the capsule, tablet, lozenge is intended for ingestion by swallowing. In another aspect, the tablet, capsule, or lozenge is orally disintegrable. In one aspect, the tablet, capsule, lozenge or troche is a slow release composition. In another aspect, the tablet, lozenge, troche or capsule is an immediate release composition. In another aspect, the oral composition can be a prepackaged liquid drink, wherein the formulation is suspended in a flavored liquid. In preferred aspects, the composition is in the form of a tablet, a capsule, or a powder meant to mix with a food, such as applesauce. Although the compositions of the disclosure are primarily oral forms, other modes of administration such as parenteral forms, or anal suppositories have been contemplated.

The tablet, capsule, and caplet forms of the disclosure may comprise, aside from those components specified above, other various additives, such as vehicle, binder, disintegrating agent, lubricant, thickener, surfactant, osmotic pressure regulator, electrolyte, sweetener, flavoring, perfume, pigment, pH regulator and others appropriately as required.

Specifically, the additives include starches such as wheat starch, potato starch, corn starch, and dextrin, sugars such as sucrose, glucose, fructose, maltose, xylose, and lactose, sugar alcohols such as sorbitol, mannitol, maltitol, and xylitol, isotransposable glycosides such as coupling sugar and paratinose, vehicles such as calcium phosphate and calcium sulfate, binders and thickeners such as starch, sugar, gelatin, gum arabic, dextrin, methyl cellulose, polyvinyl pyrrolidone, polyvinyl alcohol, hydroxy propyl cellulose, xanthan gum, pectin, tragacanth gum, casein, and alginic acid, lubricants such as leucine, isoleucine, valine, sugarester, hardening oil, stearic acid, magnesium stearate, talc, and macrogol, disintegrating agents such as avicel, CMC, CMC-Na and CMC-Ca, surfactants such as polysorbate and lecithin, and sweeteners such as sugars, sugar alcohols, aspartame, alitame, other dipeptides, stevia, and saccharin, and they may be used in proper amounts selectively in consideration of the relation with the essential components, property of the composition, manufacturing method, etc.

In another embodiment, compositions of the disclosure can optionally further comprise one or more flavoring agents. The optional flavoring agent is added to increase patient acceptability and compliance with the recommended dosing schedule. The flavoring agents that may be used include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Non-limiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including, without limitation, lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, artificial vanilla, cinnamon derivatives, and various fruit flavors, whether employed individually or in admixture. Other useful flavorings include aldehydes and esters such as cinnamyl acetate, cinnamaldehyde, citral diethylacetal, dihydrocarvyl acetate, eugenyl formate, p-methylamisol, and so forth may be used. In a specific aspect, the flavoring is spearmint oil. The flavor is optionally present from about 0.1% to about 5% by weight of the antiviral composition.

Tablets may be molded tablets or compressed tablets. Tablets may be formed by wet granulation, dry granulation, and direct compression. These techniques are known to one of skilled in the art and are described, for example, in the United States Pharmacopeia National Formulary USP XXII, 1990, pp. 1696-1697. Various other vitamins may be added to composition. Tablets may optionally further comprise flavorings or sweeteners. In one aspect, the sweetened, flavored tablet is utilized as a lozenge to be dissolved in the mouth. The compositions of the disclosure can also be prepared in a chewable form or an effervescent form. For effervescent preparations, the manufacturing method in the disclosure is basically same as in the manufacturing method of the usual effervescent preparations such as effervescent tablets. That is, components are weighed, mixed, and prepared directly by the powder compression method, dry or wet granular compression method, etc. Orally disintegrable tablets are described, for example, in U.S. Pat. No. 7,431,942, Shimuzu et al., which is incorporated herein by reference. Lozenges with a hard candy base can be prepared, for example, by the techniques of U.S. Pat. No. 6,316,008, Godfrey, which is incorporated herein by reference.

A liquid composition may further comprise other nutrients. Such liquid compositions may be prepared as described in U.S. Pat. No. 6,037,375, Sakamoto et al., which is incorporated herein by reference. A nutrient liquid composition of the disclosure contains a lysine, an ascorbic compound, a flavonoid glycoside, a threonine and a pyridoxine as essential ingredients, and is prepared in the same manner as the ordinary food and beverage, and other food materials may be appropriately added. As particularly preferred food materials, sweeteners such as organic acids and carbohydrates may be used. Organic acid components include citric acid, tartaric acid, malic acid, and succinic acid, and citric acid is particularly preferable. These organic acids are added usually in a range of 100 to 1500 mg/100 ml, preferably 250 to 800 mg/100 ml, and the composition of the material in beverage form can be prepared.

Various sweeteners can be optionally used in the tablet, liquid, capsule, lozenge or troche formulations of the disclosure. Examples of carbohydrates and sweeteners include monosaccharides such as glucose and fructose, disaccharides such as maltose, sucrose, other ordinary sugars, sugar alcohols such as xylitol, sorbitol, glycerin and erythritol, polysaccharides such as dextrin and cyclodextrin, and oligosaccharides such as fructo-oligosaccharide, galacto-oligosaccharide and lacto-sucrose. Of the carbohydrates, as the components not adversely affecting the lipid metabolism, fructose and glycerin are preferred. As oligosaccharide, addition of lacto-sucrose is preferred. A beverage composition of the disclosure can increase bifidobacteria in the body or lower the putrefaction products depending on the blend of the lacto-sucrose, so that the immune system can be intensified further. Other sweeteners include natural sweeteners such as thaumatin, stevia extract, rebaudioside A, glycyrrhizinic acid, etc. and synthetic sweeteners such as saccharin, aspartame, etc. These carbohydrates may be also added as carbohydrate mixture such as isomerized sugar and refined sugar. The sweetener is optionally present from about 0.1% to about 5% by weight of the solid composition. The blending of the carbohydrates may be about 1 to 15 g in 100 ml of the beverage composition of the disclosure, preferably about 3 to 12 g. The content of the oligosaccharide is about 0.5 to 10 g, preferably 1 to 3 g.

The nutrient liquid composition of the disclosure may also comprise, aside from the above, various nutrients, vitamins, minerals (electrolytes) including trace elements, perfumes including synthetic perfumes and natural perfumes, coloring matter, flavors (fruit, vanilla, chocolate, etc.), pectic acid and its salts, alginic acid and its salts, organic acids, thickener as protective colloidal substance, pH regulator, stabilizer, preservative, glycerins, alcohols, and sparkling component for carbonated beverages. In addition, the composition of the disclosure may also contain natural juice or fruit to be presented as fruit drink or vegetable drink. These may be used either alone or in combination of two or more kinds. The blending rate of these additives is not particularly limited, and is generally selected in a range of about 0 to 20 parts by weight to 100 parts by weight of the composition of the disclosure.

Optional additional vitamins include, whether water-soluble or fat-soluble, thiamine, niacin, retinol palmitate, bisbentiamine, riboflavin, cyanocobalamin, cholecalciferol, nicotinic acid amide, calcium pantothenate, folic acid, biotin, and choline ditartate, and those belonging to vitamin B group.

The liquid nutrient composition of the disclosure is prepared by blending these components, and the method of preparation is not particularly limited, and all components may be blended simultaneously, but more preferably fat soluble components are preliminarily dissolved in oil, and water-soluble components in water, then the solution is emulsified by using an emulsifier, so that the composition of the disclosure may be prepared. More preferably, the oil solution is added to water and a proper emulsifier to emulsify, and an aqueous solution is added and blended to the obtained emulsion. The blending operation of the components may be executed under ordinary temperature, or preferably executed by slight heating operation.

The emulsification can be executed by using a proper emulsifying machine, for example, homo-mixer or high pressure homogenizer, either by complete passing system or by circulation system. The emulsion after emulsification is filtered by conventional process, and poured into proper containers and sterilized, so that a desired beverage product is obtained. Sterilization may be effected by heating, aseptic filtering, etc.

To prepare the composition of the disclosure as a carbonated beverage, carbon dioxide may be injected into the emulsifier by conventional process. Such beverage is preferred to be prepared in the osmotic pressure range of about 260 to 600 mOsm/kg.

The liquid composition of the disclosure may be also prepared in an effervescent form. The effervescent form should contain, aside from the essential components of the disclosure, proper amounts of sodium carbonate and/or sodium hydrogen carbonate and neutralizing agent as foaming components. The neutralizing agent used herein is an acidic compound capable of generating carbon dioxide by neutralizing sodium carbonate or sodium hydrogen carbonate. Such compound includes, for example, L-tartaric acid, citric acid, fumaric acid, ascorbic acid and other organic acid. Preferred ascorbic acid possesses both the action of neutralizing agent and the action of antioxidant.

It has surprisingly been found that compositions of the present disclosure inhibit influenza A viral replication in MDCK cells in vitro. QuantiGene Plex 2.0 assay utilizing branched DNA (bDNA) signal amplification and multi-analyte profiling beads (xMAP®) technologies was used to enable the detection and quantitation of influenza A mRNA. In particular, Formula V was found to decrease influenza A mRNA more effectively than other known formulations such as Formula A2. In another embodiment, the disclosure provides a method to decrease viral activity and/or to reduce viral replication comprising treating a virus-infected cell with a composition comprising a lysine, an ascorbic compound, a flavonoid glycoside, a threonine and a pyridoxine, in an effective amount.

Neuraminidase (also known as sialidase) is a very common enzyme that hydrolyzes terminal sialic acid residues on polysaccharide chains, most often exposing a galactose residue. Although neuraminidase is found in mammals, it is predominantly expressed in microorganisms such as bacteria and viruses. J. Biochem. Biophys. Methods 22, 23 (1991). The negative-stranded RNA influenza virus contains two surface glycoproteins, hemagglutinin (HA) and neuraminidase. Neuraminidase is thought to play a key role in the invasion of target cells and the subsequent replication of the influenza virus through its cleavage of target cell receptor sialic acid moieties. This action prevents further interaction of the virus with the target cell and facilitates elution of progeny virions from the infected cell (Haskell et al., Neuraminidase inhibition and viral chemotherapy. J. Med. Chem. 13, 697 (1970); McKimm-Breschkin, Resistance of influenza viruses to neuraminidase inhibitors—a review. Antiviral Res. 47, 1 (2000)). Additionally, newly synthesized neuraminidase and HA on virions may also contain sialic acid residues that can be cleaved by neuraminidase in order to prevent self-aggregation. It is also thought that the penetration of mucosal linings by the virus is enhanced by neuraminidase hydrolytic action on fetuin, a major component of these membranes. These essential activities make neuraminidase an important target for influenza drug development. Neuraminidase activity can be determined by use of a commercially available kit such as, for example, the Molecular Probes Amplex® Red Neuraminidase assay kit No. A22178 as used according to protocol, which is incorporated herein by reference.

Yeo et al. investigated the effect of influenza A/Beijing/353/89 (H3N2) virus infection on the expression of type IV collagenase in two different types of epithelial cells (Yeo et al. Influenza A virus infection modulates the expression of type IV collagenase in epithelial cells. Arch. Virol. 144: 1361-1370 (1999)). Depending on the cell line infected, the viral infection caused changes in the expression of type IV collagenase. The expression of matrix metalloproteinase-9 (MMP-9; 92 kDa) but not of matrix metalloproteinase-2 (MMP-2; 72 kDa) was stimulated in Vero cells. In MDCK cells, the MMP-2 production increased with the virus infection. The MMP-9 and -2 expression by influenza A virus infection were determined to be modulated at transcriptional level, depending on the epithelial cell line. Therefore, formulations which inhibit expression of MMP-9 and/or MMP-2 may be of some interest as they may possess or enhance antiviral activity. It should be noted, however, that strong inhibition of these enzymes in pregnancy may not be desirable.

In one embodiment, certain compositions of the disclosure were shown to inhibit neuraminidase in a dose-dependent fashion surprisingly better than known compositions. Results are shown in FIGS. 3-6. Formula V was found to inhibit neuraminidase more effectively than other known formulations such as Formula A2.

In one embodiment, the disclosure provides a method to decrease viral activity comprising treating a virus-infected cell with a composition known to inhibit neuraminidase activity and/or only weakly inhibit MMP-9 expression, comprising a lysine, an ascorbic compound, a flavonoid glycoside, a threonine and a pyridoxine, in an effective amount. In one aspect, a method for the treatment or prophylaxis of a viral infection in a subject comprises administration to the subject a therapeutically effective amount of a composition comprising a lysine, an ascorbic compound, a flavonoid glycoside, a threonine, and a pyridoxine. One key advantage of the compositions of the present disclosure is the ability to decrease viral activity in a non-strain specific manner.

EXAMPLES

Example 1. Virus Production Protocol

Madin-Darby canine kidney (MDCK) cells (ATCC) were maintained in minimum essential medium (MEM) with Earle's salts (Gibco BRL, Grand Island, N.Y.) supplemented with 2 mM L-glutamine, 100 U/ml penicillin, 100 g/ml streptomycin and 10% heat inactivated fetal calf serum, (Hyclone)) and buffered by the addition of HEPES buffer solution (pH 7.55, 10 mM final concentration, Invitrogen).

The African Green Monkey kidney cell line Vero (ATCC) was maintained in minimum essential medium (MEM) with Earle's salts (Invitrogen) supplemented with 2 mM L-glutamine, 100 U/ml penicillin, 100 g/ml streptomycin and 10% heat inactivated fetal calf serum, (Hyclone).

The H1N1 influenza strain A/WS/33 (ATCC) was used to generate high titer viral stocks by passage in MDCK cells.

Example 2. In Vitro bDNA Assay for Influenza A mRNA Activity

MDCK or Vero cells were plated at $1e^5$ cells/mL in a 100 uL volume in tissue culture treated 96 well plates. The following day cells were infected with virus at a multiplicity of infection of 10 and viral activity was measured. For testing compounds, cells were preincubated with compound 1 hr prior to infection.

All formulations were run in triplicate for each concentration. Test formulations are shown in Example 5, Table 1. It should be noted that Formula A1 is Airborne® effervescent health formula and Formula T is Tamiflu®.

After overnight incubation, the cells were harvested, lysed, and supernatants were subjected to QuantiGene Plex 2.0 assay (Panomics, Inc., Fremont, Calif.) for quantitative assay of influenza A mRNA according to manufacturer's protocol. The QuantiGene Plex 2.0 assay combines branched DNA (bDNA) signal amplification and multi-analyte profiling beads (xMAP®) technologies to enable the detection and quantitation of multiple mRNA targets simultaneously. Generally, this assay is considered faster than traditional methods used to monitor influenza infection which typically require 2-5 days to perform.

The bDNA assay is a hybridization-based method of target-specific RNA quantitation that amplifies signal rather than target RNA, using labeled DNA probes. The QuantiGene Plex 2.0 system utilizes fluorescent microspheres (Capture Beads) as a support to capture specific RNA molecules. The ability to quantify multiple target-specific RNA molecules in a single sample lies in the design of the Probe Sets. For each RNA molecule of interest, an oligonucleotide Probe Set containing three types of synthetic probes, Capture Extenders (CEs), Label Extenders (LEs), and Blockers (BLs) that hybridize and span contiguous sequences of the target RNA, is provided. The CEs discriminate among the different Capture Beads within the bead array while capturing, via cooperative hybridization, the target RNA.

Signal amplification is mediated by DNA amplification molecules that hybridize to the tails of the LEs. Each amplification unit contains multiple hybridization sites for biotinylated Label Probes that bind Streptavidin-conjugated R-Phycoerythrin (SAPE). The resulting fluorescence signal associated with individual Capture Beads is read on a Luminex flow cytometer. Signal is reported as median fluorescence intensity (MFI) and is proportional to the number of target RNA molecules present in the untreated sample.

Figure 2:
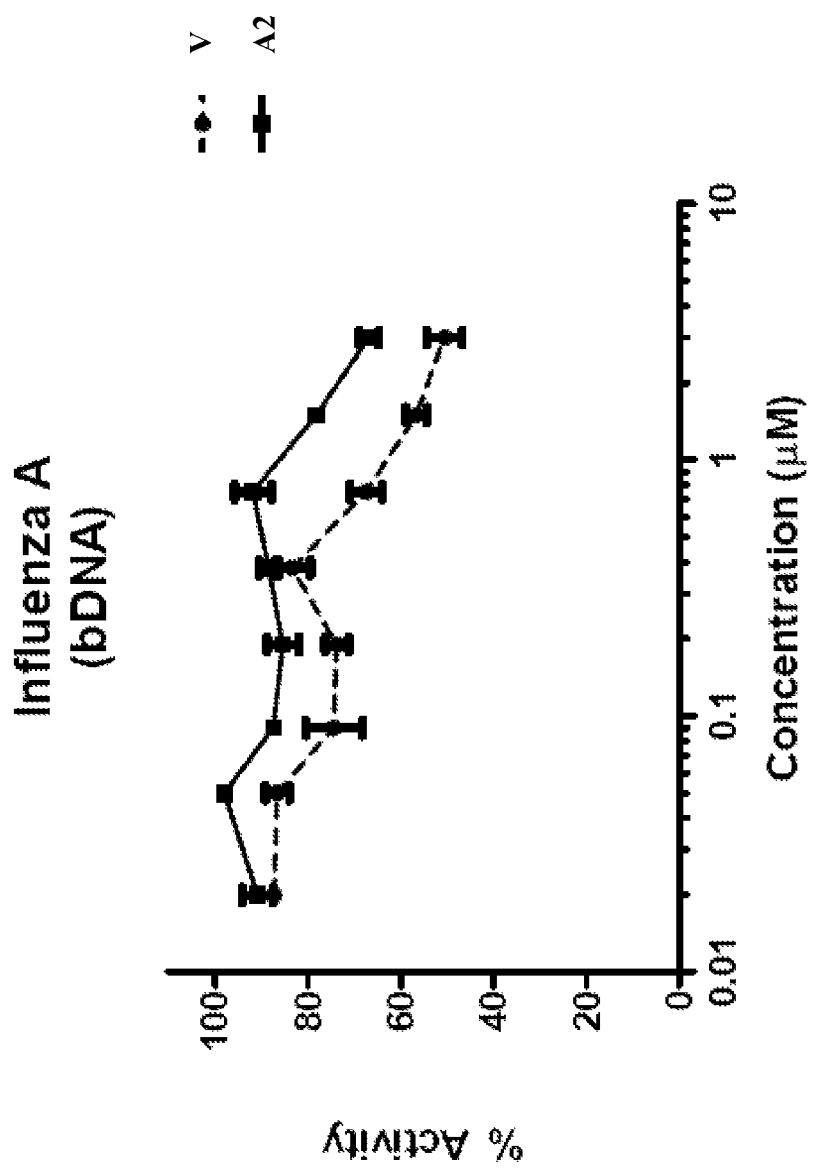
Figure 3:
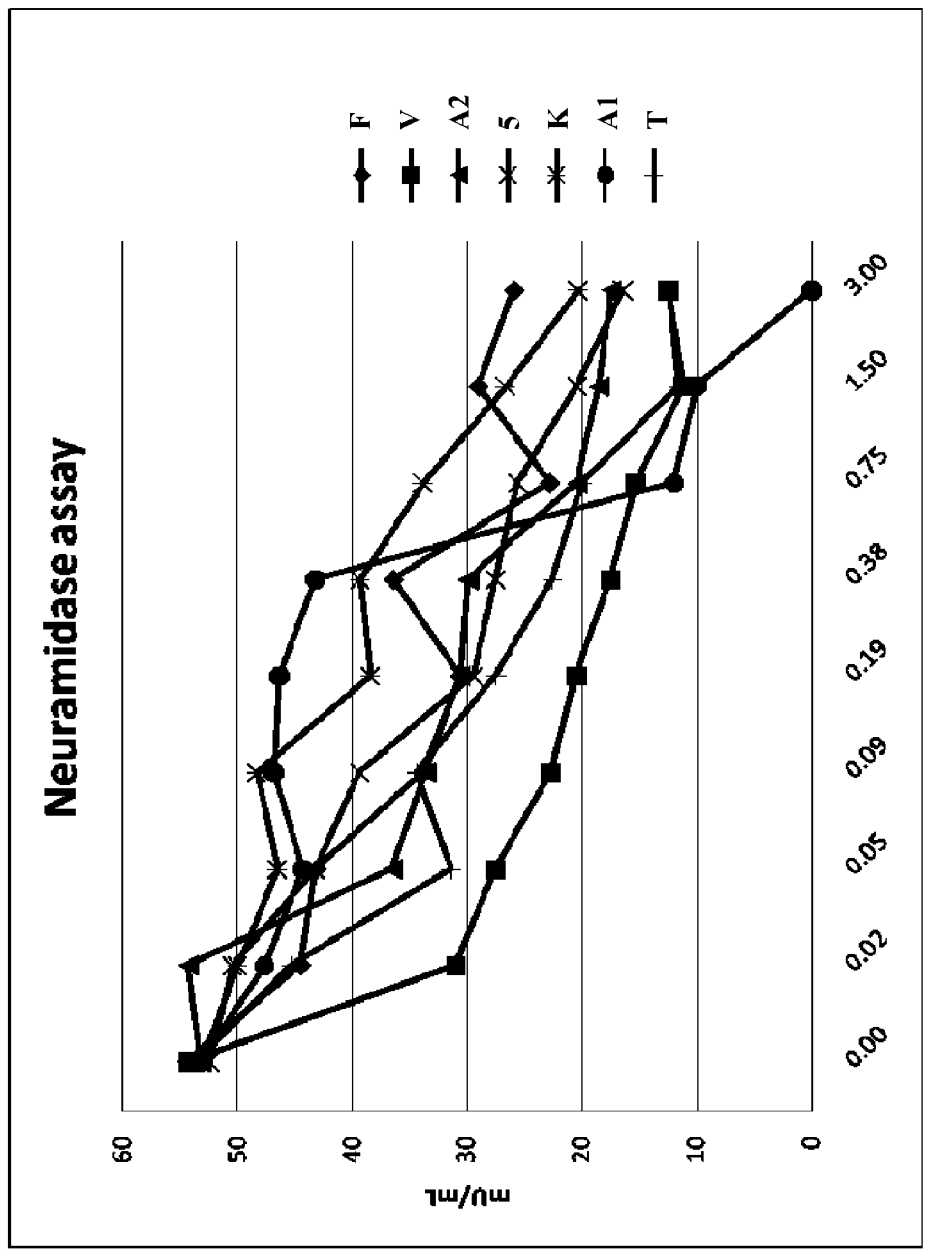
Figure 4:
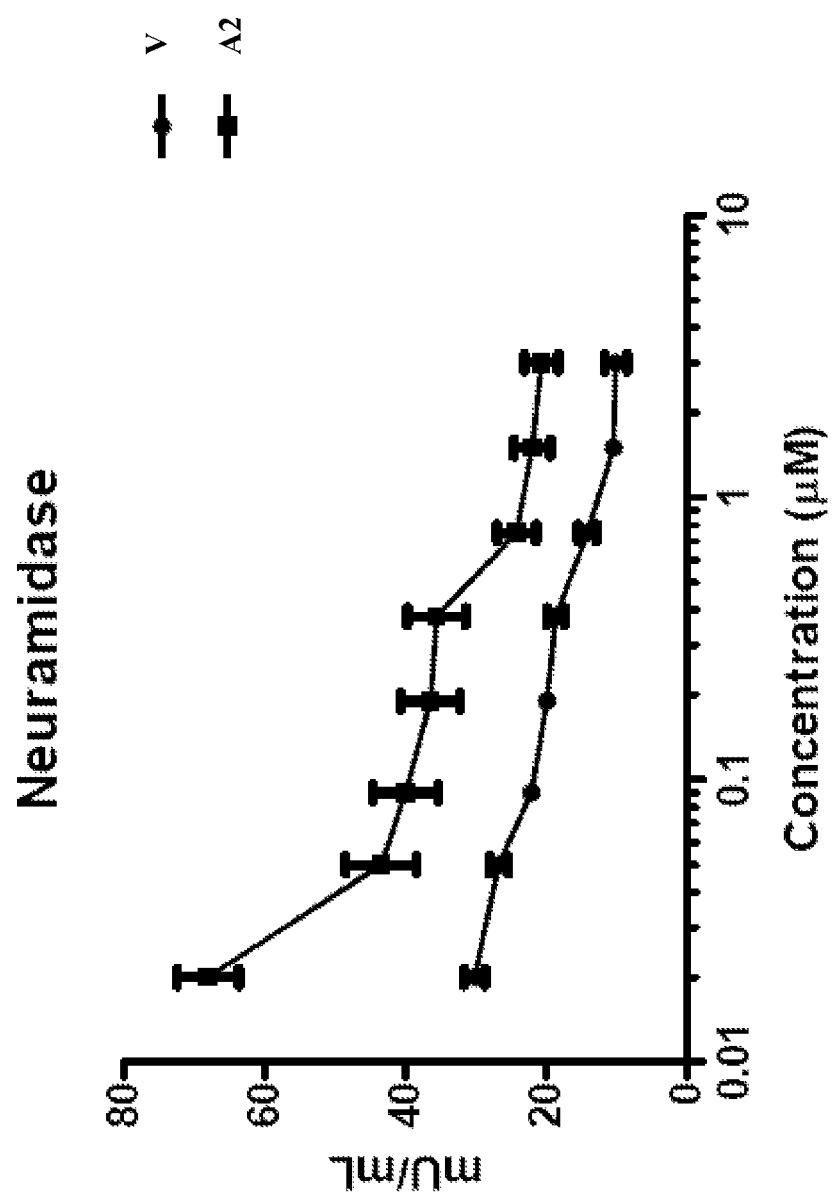

Results for influenza A-infected Vero cell supernatants are shown in FIGS. 1 and 2. In FIG. 1, Formula V and Formula 5 decreased the amount of influenza A mRNA in a dose dependent manner. Although Formula A1 decreased the amount of amount of influenza A mRNA at high doses, it is interpreted that the effervescent chemicals used to buffer the Formula A1 commercial product increased the pH resulting in suppression by pH effect at the higher concentrations of Formula A1. A1 was also found to be cytotoxic at the high doses. Formula V appeared more potent than Formula A2 in this assay as shown in FIG. 2. Concentrations are expressed in micromolar (μM) concentrations.

Example 3. In Vitro Molecular Probes Amplex® Red Neuraminidase (Sialidase) Assay The Molecular Probes Amplex® Red Neuraminidase assay kit No. A22178 was used according to manufacturer's protocol, which is incorporated herein by reference.

The Molecular Probes Amplex® Red Neuraminidase assay utilizes Amplex Red to detect $H_2O_2$ generated by galactose oxidase oxidation of desialiated galactose, the end result of neuraminidase action. The $H_2O_2$ then, in the presence of horseradish peroxidase (HRP), reacts with a 1:1 stoichiometry with Amplex Red reagent to generate the red-fluorescent oxidation product, resorufin. (Mohanty et al. A highly sensitive fluorescent micro-assay of $H_2O_2$ release from activated human leukocytes using a dihydroxyphenoxazine derivative. J. Immunol. Methods 202, 133 (1997)). Resorufin has absorption and fluorescence emission maxima of approximately 571 nm and 585 nm, respectively, and because the extinction coefficient is high (54,000 $cm^{-1}M^{-1}$), the assay can be performed either fluorometrically or spectrophotometrically.

MDCK or Vero cells were plated at $1e^5$ cells/mL in a 100 uL volume in tissue culture treated 96 well plates. The following day cells were infected with virus at a multiplicity of infection of 10 and viral activity was measured. For testing compounds, cells were preincubated with compound 1 hr prior to infection. After overnight incubation, the cells were harvested, lysed, and supernatants were subjected to assay.

All formulations were run in triplicate for each concentration. Test formulations are shown in Table 1. It should be noted that Formula A1 is Airborne® effervescent health formula and Formula T is Tamiflu®.

Results for influenza A-infected Vero cell supernatants are shown in FIGS. 3 and 4. Formula V is shown to be effective at inhibition of the neuraminidase enzyme in a dose-dependent manner. Although Formula A1 seemed to be active at high doses, it is likely that the effervescent chemicals used to buffer the commercial product (Airborne®) increased the pH in the assay and resulted in suppression via a pH effect only at the higher concentrations of Formula A1. Formula A1 also exhibited cytotoxicity at high doses.

Example 4. In Vitro Inhibition of Matrix Metalloproteinase 9 (MMP-9)

A Quantikine Human MMP-9 (total) Immunoassay Assay, R&D Systems, was used to quantify expression of MMP-9 in infected cells according to the manufacturer's protocol, which is incorporated herein by reference.

Vero cells were plated at $1e^5$ cells/mL in a 100 uL volume in tissue culture treated 96 well plates. The following day cells were infected with virus at a multiplicity of infection of 10 and viral activity was measured. For testing compounds, cells were preincubated with compound 1 hr prior to infection. After overnight incubation, the cells were harvested, lysed, and supernatants were subjected to assay.

This MMP-9 assay employs the quantitative sandwich enzyme immunoassay technique. A monoclonal antibody specific for MMP-9 has been pre-coated onto a microplate. Standards and samples are pipetted into the wells, and MMP-9 is bound by the immobilized antibody. After washing away unbound substances, an enzyme-linked polyclonal antibody specific for MMP-9 is added to the wells. Following a wash to remove unbound antibody-enzyme reagent, a substrate solution is added to the wells and color develops in proportion to the amount of total MMP-9 (pro and/or active) bound in the initial step. The color development is stopped and the intensity of the color is measured.

Test formulations are shown in Example 5, Table 1. It should be noted that Formula A1 is Airborne® effervescent health formula and Formula T is Tamiflu®. Results for influenza A-infected Vero cell supernatants are shown in FIGS. 5 and 6. It is interpreted that the effervescent chemicals used to buffer the Formula A1 commercial product increased the pH in the assay and interfered with the assay via a pH effect only at the higher concentrations of Formula A1.

Formula V weakly inhibited expression of MMP-9 in a dose-dependent manner. Formula T (Tamiflu®) exhibited pronounced dose-dependent inhibition of expression of MMP-9. It is believed that the distinctly weaker inhibition of MMP-9 expression exhibited in the presence of Formula V may result in a decreased risk during pregnancy compared to treatment of a viral infection with Tamiflu® in a pregnant woman.

Example 5. In Vitro Inhibition of Matrix Metalloproteinase 2 (MMP-2)

Two separate kits were employed to determine if the formulations of the disclosure inhibit expression of MMP-2. The Calbiochem® MMP-2 ELISA kit is a non-isotopic immunoassay for the in vitro quantification of human MMP-2 protein in tissue culture medium. The R&D Systems Quantikine® MMP-2 (total) Immunoassay kit is used for the quantitative determination of active and pro-Matrix Metalloproteinase 2 (total MMP-2) concentrations in cell culture supernates. All formulations were run in triplicate utilizing each of the two assay kits. No formulation of the present disclosure significantly inhibited MMP-2 expression when tested in various concentrations up to about 5 µM.

Example 6. Formulations. Powder Formulations

Ingredients for various test formulations are shown in Table 1; the amounts for a single dose packet of powder are shown. A test batch for each formulation was prepared utilizing five times the amounts shown. Each ingredient was added to the batch and the batch was mixed thoroughly, divided by weight and sealed into five packets. Alternatively, the powder can be filled to hard shell capsules.

TABLE 1

Formulations- weight per dose for powder formulation.

| Material | Amount (grams) | | | | |
|---|---|---|---|---|---|
| | Formula V | Formula F | Formula 5 | Formula K | Formula A2 |
| L-Lysine HCl | 3.00 | 3.00 | 3.00 | 3.00 | 1.00 |
| Proline | | | | | 0.75 |
| Arginine | | | | | 0.50 |
| Threonine | 0.05 | 0.06 | 0.05 | 0.05 | |
| Acetyl-L-cysteine | | | | 0.20 | 0.20 |
| Selenomethionine | | | | | 0.01 |
| Ascorbic acid | 0.28 | 1.00 | 0.45 | 0.20 | 0.71 |
| Calcium ascorbate | 0.64 | | 0.64 | 0.64 | 0.02 |
| Magnesium ascorbate | | | | | 0.05 |
| Niacinamide ascorbate | 0.30 | | | 0.42 | |
| Ascorbyl palmitate | 0.05 | | 0.05 | 0.05 | |
| Green tea extract (90% polyphenols) | | | | | 1.0 |
| Hesperidin complex | 0.30 | 0.33 | 0.30 | 0.30 | |
| Rutin NF | 0.30 | 0.33 | 0.30 | 0.30 | |
| Pyridoxine HCl | 0.05 | 0.05 | 0.05 | 0.05 | |
| Taurine | 0.20 | 0.04 | 0.20 | | |
| Copper gluconate | | | | | 0.02 |
| Manganese gluconate dihydrate | | | | | 0.01 |
| Pectin (87% galacturonic acid) | | 0.33 | | | |
| Total weight per packet (g) | 5.17 | 5.14 | 5.03 | 5.20 | 4.23 |

Example 7. Formulations. Tablet Formulations

Tablet formulations were prepared using the ingredients shown in Table 2. The amount of ingredient shown is equal to one dose. Five tablets contained one dose of the formulation. A wet granulation technique was employed and compressed tablets were coated with a white coating shown in Table 2. Tablets were dried and stored at room temperature.

TABLE 2

Tablet Formulations- amount per tablet.

| Ingredient | Formula FT (mgs) | Formula VT (mgs) |
|---|---|---|
| Citrus Bioflavonoid (Hesperidin) 98% | 142.97 | 66.60 |
| Methocel E-5 HPMC | 4.42 | 5.00 |
| L-Lysine Monohydrate | 612.20 | 600.00 |
| Ascorbic Acid | 218.80 | 200.00 |
| Rutin NF | 30.00 | 66.00 |
| Pectin | 30.00 | 66.00 |
| Pyridoxine HCl USP Vit B6 | 13.40 | 10.00 |
| Taurine | 8.20 | 8.00 |
| L-Threonine | 12.20 | 12.00 |
| Microcrystalline Cellulose | 200.00 | 200.00 |
| Croscarmellose Sodium | 20.00 | 20.00 |
| Silica | 6.00 | 6.00 |
| Magnesium Stearate | 10.00 | 10.00 |
| Riboflavin Vit B2 | 1.50 | 0 |
| Purified Water | | |
| White Coating including: Dextrin Dextrose Hypermellos Mineral Oil Polyethylene Glycol Polysorbate 80 Croscarmellose Sodium Sodium Citrate Titanium Dioxide | 40.00 | 40.00 |
| Total Mgs: | 1349.69 | 1308.82 |

Example 8. Preliminary Clinical Data

A preliminary trial was performed during an influenza A outbreak. Subjects were given the tablet Formulation FT of Example 6, wherein 5 tablets equaled one dose. Study subjects were instructed to take one dose at the first sign of flu-like symptoms; and repeat dosing every 4 to 6 hours until symptoms resolved. Subjects swallowed each dose with water. Fourteen patient surveys were completed. Subjects reported flu-like symptoms as shown in Table 3. In addition, certain patients also exhibited additional symptoms of dry cough, sore throat, or headache.

TABLE 3

Preliminary Clinical Surveys.

| Patient No. | Age | Gender | | Symptoms | | | Duration of Symptoms (hours) |
|---|---|---|---|---|---|---|---|
| | | F | M | Body Aches | Fatigue | Fever | |
| 1 | 42 | 1 | 0 | 1 | 1 | 0 | 1.5 |
| 2 | 21 | 0 | 1 | 0 | 0 | 1 | 2 |
| 3 | 49 | 0 | 1 | 1 | 1 | 1 | 1.5 |
| 4 | 85 | 0 | 1 | 1 | 0 | 1 | 2 |
| 5 | 27 | 0 | 1 | 1 | 1 | 1 | 2 |
| 6 | 26 | 1 | 0 | 1 | 1 | 1 | 1 |
| 7 | 17 | 1 | 0 | 0 | 1 | 1 | 2 |
| 8 | 54 | 1 | 0 | 0 | 1 | 0 | 1.5 |
| 9 | 49 | 1 | 0 | 1 | 1 | 1 | 3.5 |
| 10 | 52 | 1 | 0 | 1 | 1 | 1 | 4.5 |
| 11 | 22 | 1 | 0 | 1 | 1 | 1 | 5 |
| 12 | 43 | 0 | 1 | 1 | 1 | 1 | 12 |
| 13 | 61 | 0 | 1 | 1 | 1 | 1 | 13 |
| 14 | 54 | 1 | 0 | 1 | 1 | 1 | 18 |
| Average | 42 | 8 | 6 | 11 | 12 | 12 | 4.97 |
| Std. Dev. | 19 | | | | | | 5.36 |

Eight subjects reported resolution of symptoms within about 2 hours after taking the first dose of the formula. Three more subjects reported complete resolution of symptoms within about 6 hours after the first of two doses. Three more subjects reported resolution within about 18 hours after the first of three to four doses.

Example 9. Prophylactic Dosing

In an anecdotal study, two subjects working in a vision center on a daily basis were asked not to get a flu vaccine last season but to take a single daily prophylactic dose of Formula F at 40% strength (2 tablets per dose). Each subject reported that a co-worker had contracted influenza during this time. The area in which the subjects live and work experienced a major outbreak of influenza A, with two local hospitals banning visitors during the outbreak. Neither subject contracted influenza.

Example 10. Neuraminidase Assay of Formulation Components

In order to determine the relative contribution of each component in the compositions of the disclosure and identify additive and synergistic effects, each component of interest was evaluated in various combinations in the Neuraminidase Assay in a manner similar to Example 3. The test compositions were assayed in an in vitro assay to measure neuraminidase activity on influenza A infected MDCK cells. Madin Darby Canine Kidney (MDCK) epithelial cells were obtained from the ATCC (Manassas, Va.) and grown as described by the vendor. Cells were infected with human influenza virus (TC-adapted strain A/WS/33, ATCC-1520) and propagated as described previously. This strain demonstrates cross reaction with PR8 and swine influenza virus according to the ATCC. To measure neuraminidase activity, viral stocks were used to infect MDCK cells and neuraminidase activity was quantified using the Amplex Red Neuraminidase assay kit (Invitrogen, Inc. Carlsbad Calif.). Briefly, MDCK cells were infected with influenza A virus at 37° C. in the presence of the compositions shown in Table 4. Each condition was assayed in triplicate over an 8 point 2 fold dilution series. The Amplex Red method of quantifying neuraminidase activity uses three different enzymes: NA, galactose oxidase and horseradish peroxidase. The combined action of peroxide and HRP, Amplex Red is oxidized to liberate resorufin and read on a spectrophotometer at OD 563 nm.

Oseltamivir carboxylate was used as a standard neuraminidase inhibitor (NAI) positive control for comparison. Tamiflu® (Oseltamivir phosphate) is an ethyl ester prodrug requiring ester hydrolysis for conversion to the active form, oseltamivir carboxylate. Oseltamir carboxylate is an inhibitor of influenza virus neuraminidase affecting release of virus particles.

FIG. 7, Table 4, shows the various compositions that were tested in the neuraminidase assay. Each test composition was compared to Formula V and to oseltamivir carboxylate in the neuraminidase assay. FIGS. 8-13 show the activity of various compositions in the neuraminidase assay. The concentration shown in the x-axis of the FIGS. 8-13 represents either the L-lysine HCl concentration in each test composition and in Formula V, or the oseltamivir carboxylate concentration.

Figure 8:
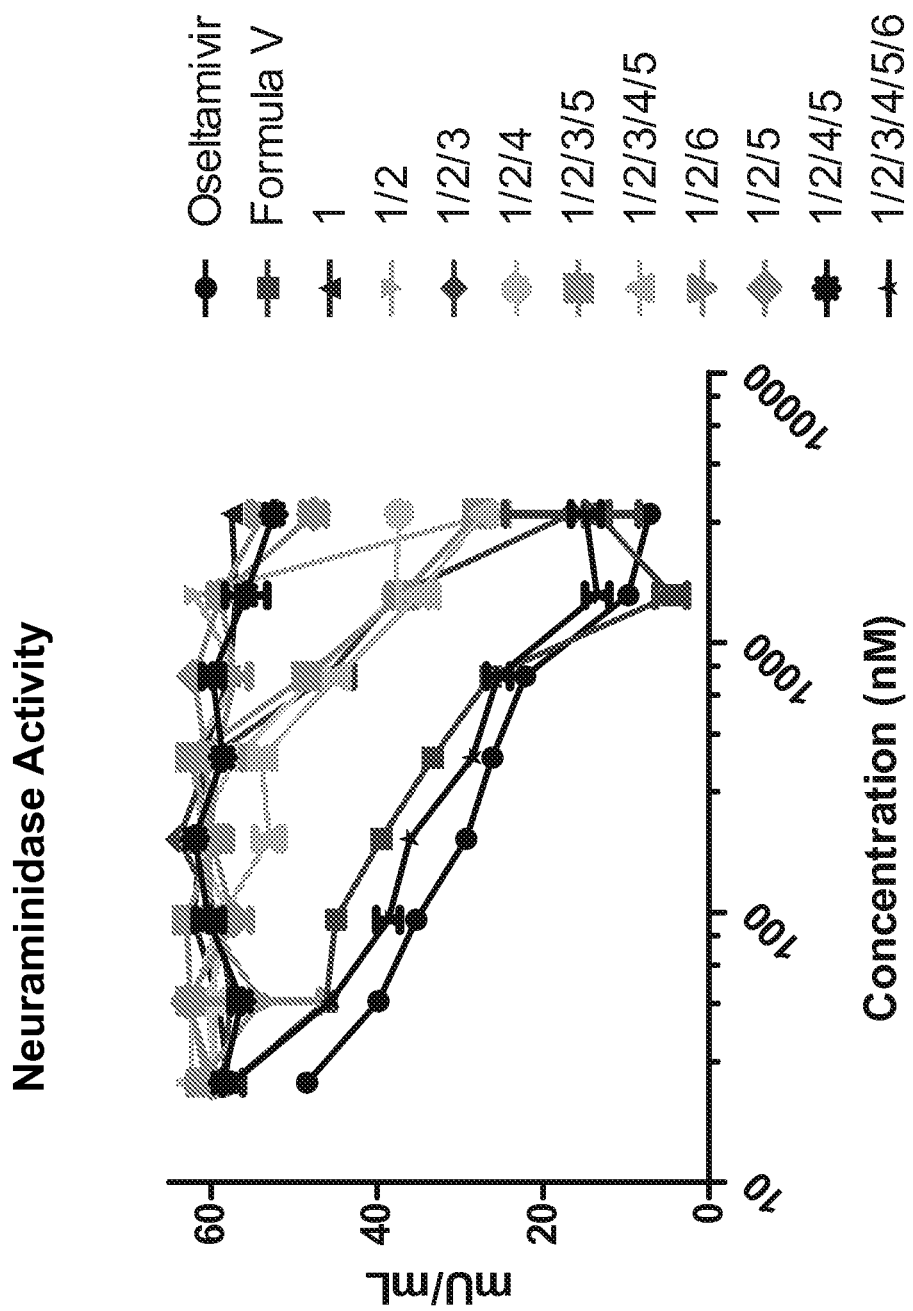

FIG. 8 shows an overlay of the neuraminidase activity of human influenza virus infected cells after exposure to oseltamivir carboxylate, Formula V and ten test compositions containing various components of Formula V. The numbers 1-6 are used to identify individual major components of Formula V. All six components, lysine, ascorbic acid/ascorbates, flavonoid glycosides, pyridoxine, threonine and taurine are necessary for full synergistic inhibition of neuraminidase activity.

Figure 9:
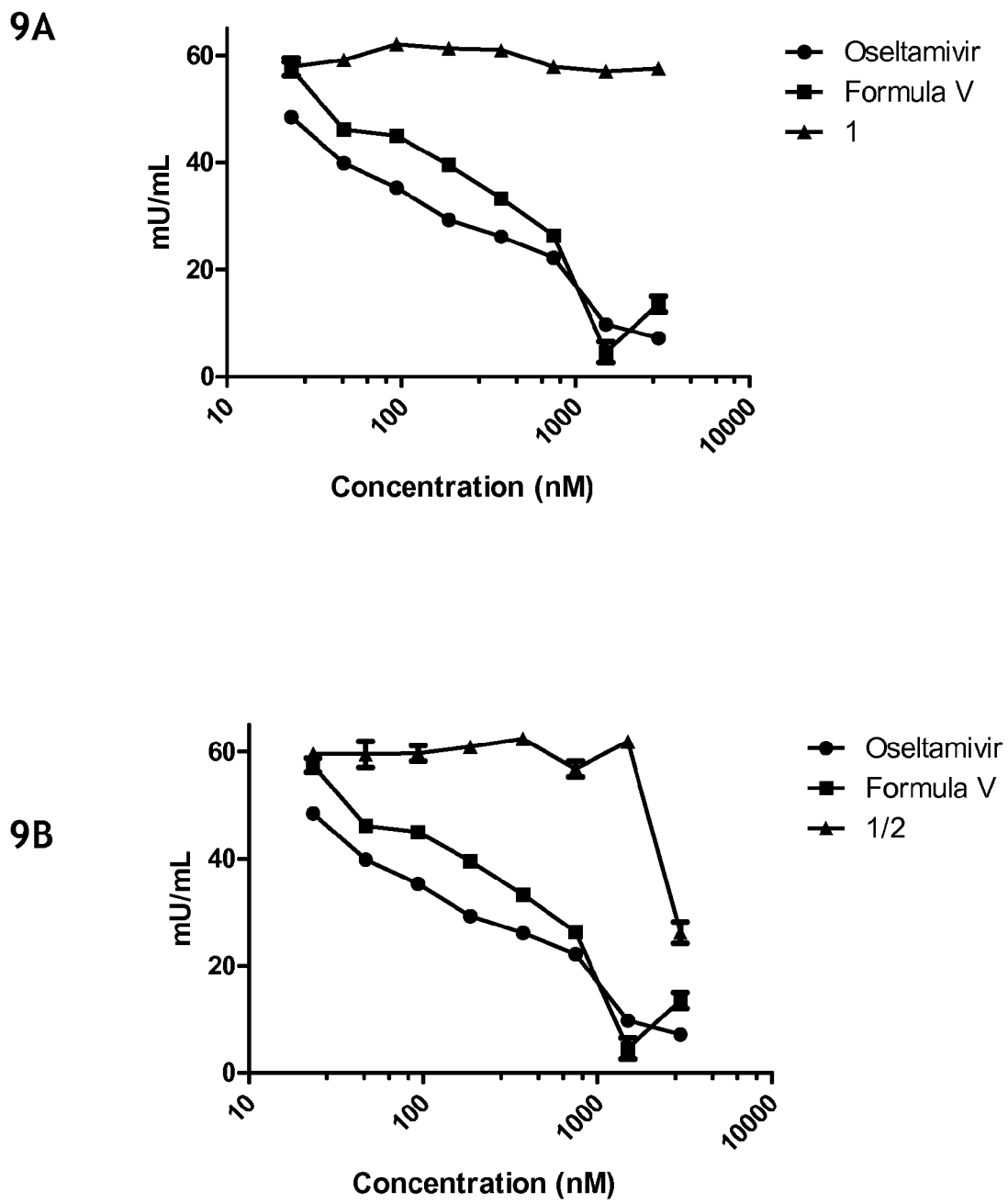

FIG. 9 shows neuraminidase activity of human influenza virus infected cells after exposure to oseltamivir carboxylate, Formula V and either lysine alone (1) or lysine with ascorbic acid/ascorbates (1/2; 9A). Neither test composition is very effective until the highest concentration of lysine/ascorbates (1/2; 9B) is employed.

Figure 10:
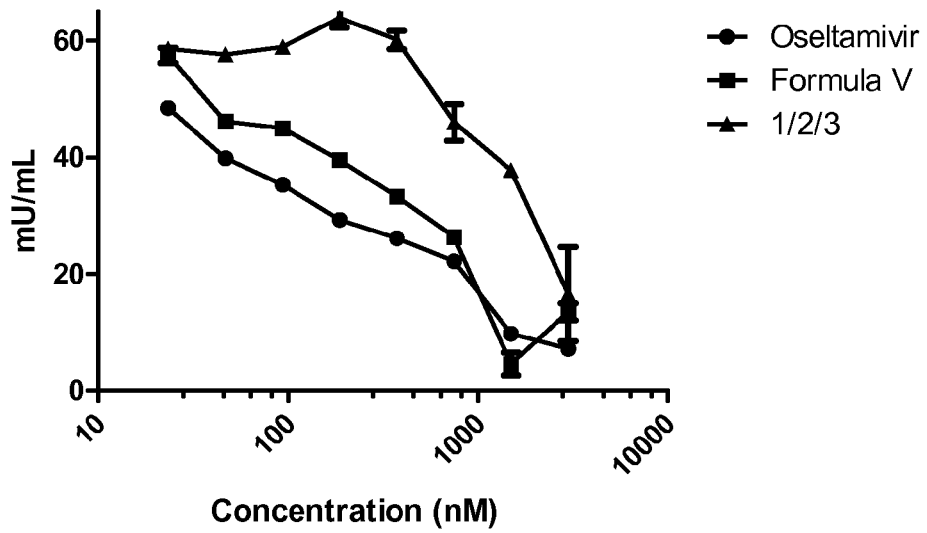
Figure 10:
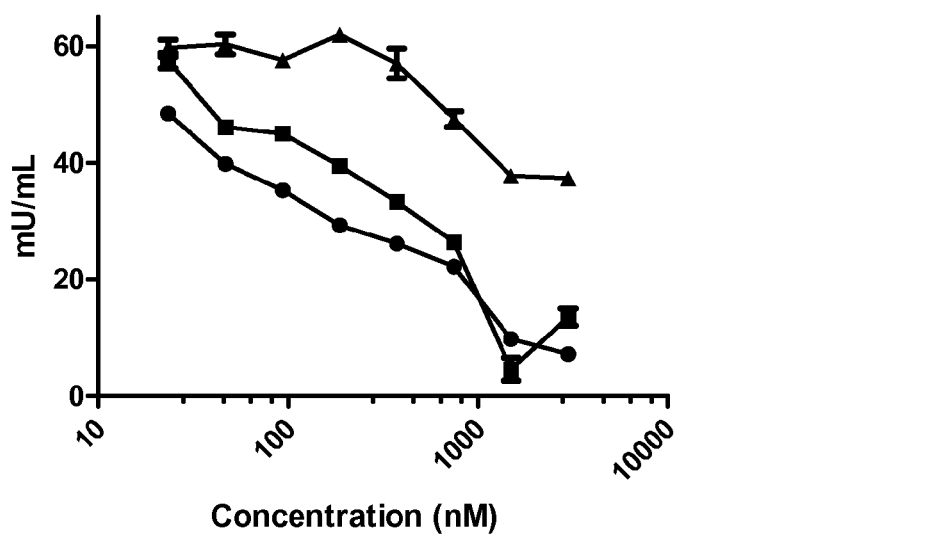

FIG. 10 shows neuraminidase activity of human influenza virus infected cells after exposure to oseltamivir carboxylate, Formula V and either lysine/ascorbates/flavonoid glycosides (1/2/3; 10A) or lysine/ascorbates/pyridoxine (1/2/4; 10B). Some dose-dependent decrease in neuraminidase activity is seen with the formulation of lysine/ascorbates/flavonoid glycosides (1/2/3) at the four highest concentrations. A weaker dose-dependent decrease in neuraminidase activity is seen with the formulation of lysine/ascorbates/pyridoxine (1/2/4) at the four highest concentrations.

Figure 11:
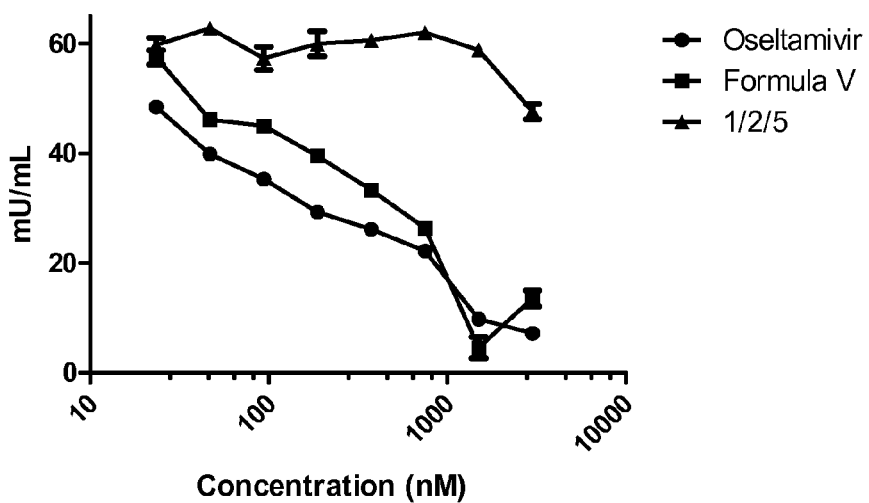
Figure 11:
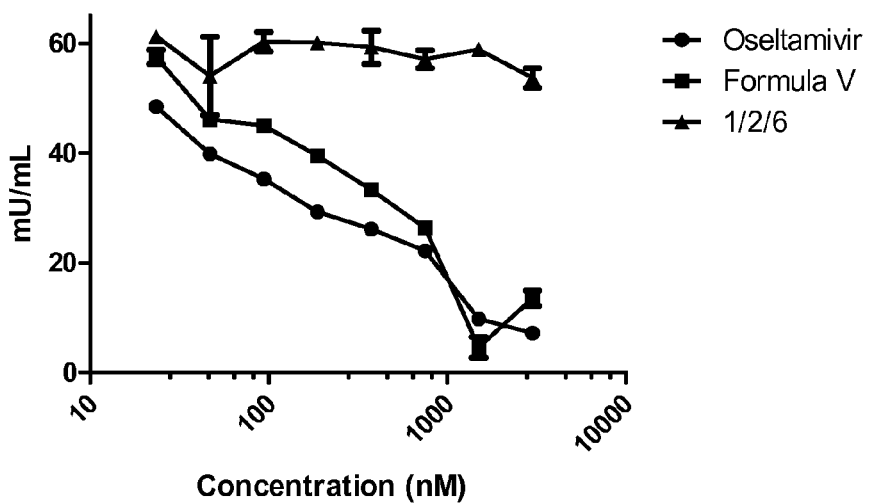

FIG. 11 shows neuraminidase activity of human influenza virus infected cells after exposure to oseltamivir carboxylate, Formula V and either lysine/ascorbates/threonine (1/2/5; 11A) or lysine/ascorbates/taurine (1/2/6; 11B). A weak decrease in neuraminidase activity is seen with lysine/ascorbates/threonine at higher concentrations.

Figure 12:
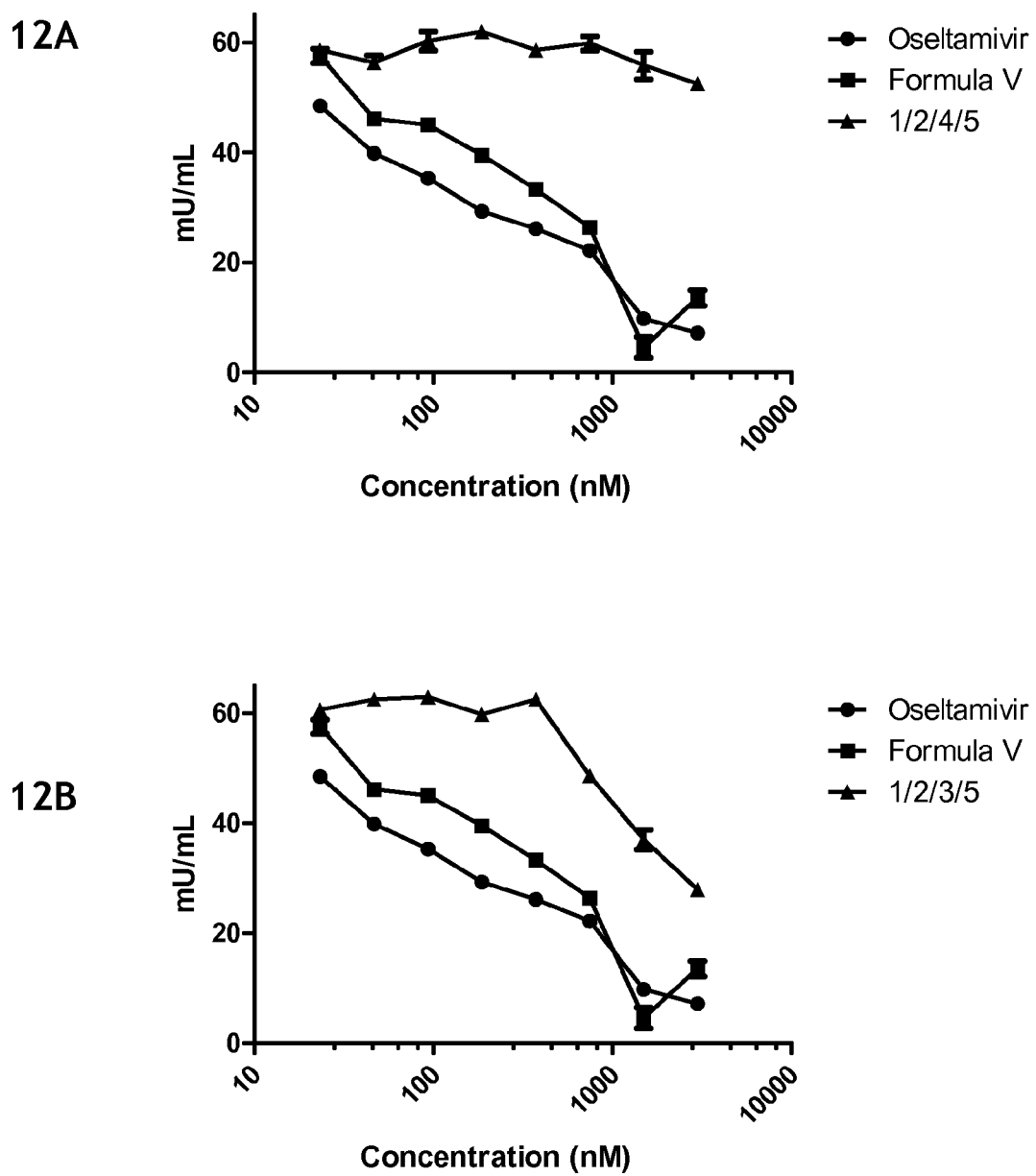

FIG. 12 shows neuraminidase activity of human influenza virus infected cells after exposure to oseltamivir carboxylate, Formula V and either lysine/ascorbates/pyridoxine HCl/threonine (1/2/4/5; 12A) or lysine/ascorbates/flavonoid glycosides/threonine (1/2/3/5; 12B). The composition of lysine/ascorbates/flavonoid glycosides/threonine exhibits a dose dependent decrease in neuraminidase activity at the three highest concentrations.

Figure 13:
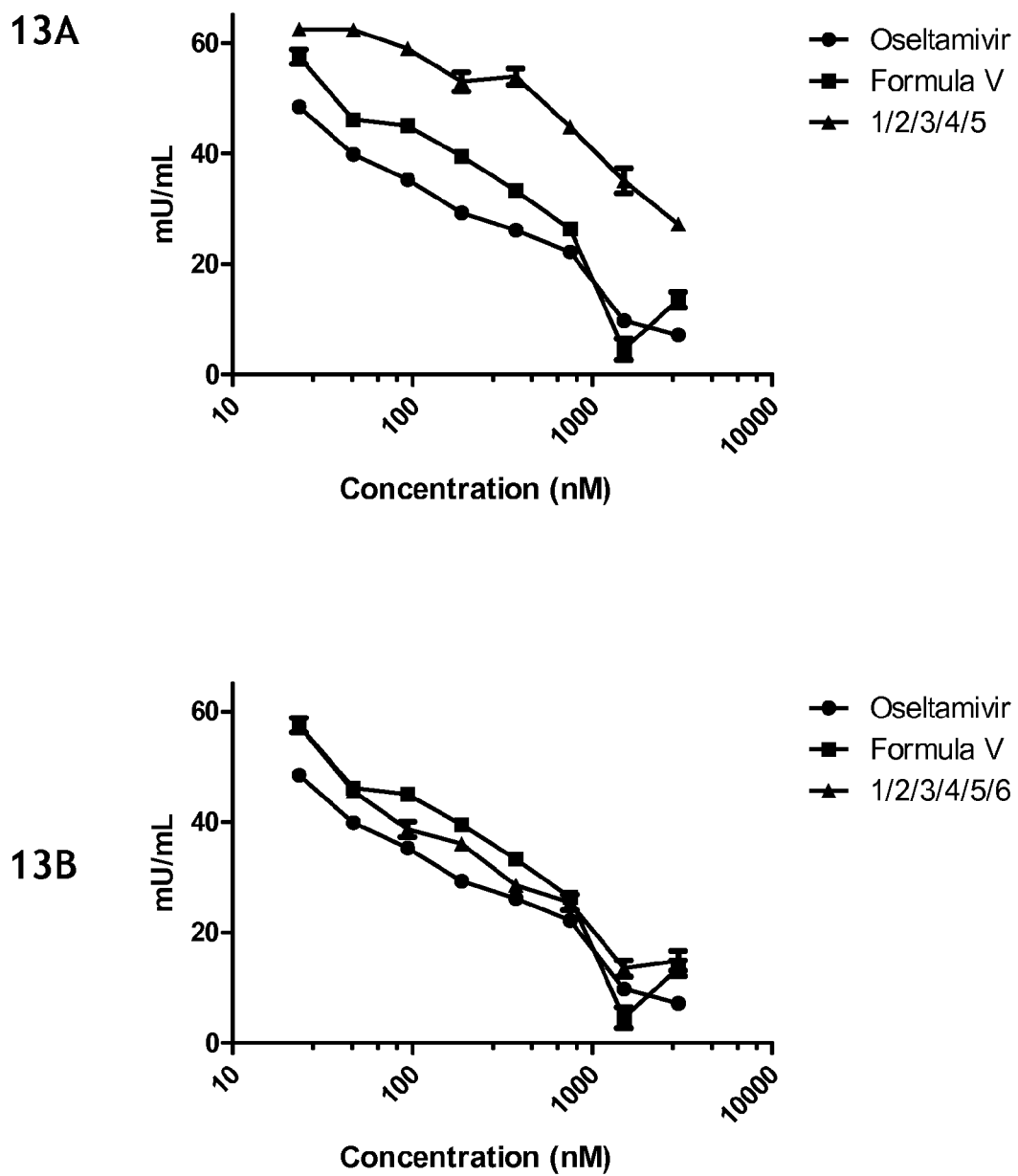

FIG. 13 shows neuraminidase activity of human influenza virus infected cells after exposure to oseltamivir carboxylate, Formula V and either lysine/ascorbates/flavonoid glycosides/pyridoxine HCl/threonine (1/2/3/4/5; 13A) or lysine/ascorbic acid/flavonoid glycosides/pyridoxine HCl/threonine/taurine (1/2/3/4/5/6; 13B). Both compositions produce a robust, dose dependent decrease in neuraminidase activity. However, only the composition of lysine/ascorbic acid/flavonoid glycosides/pyridoxine HCl/threonine/taurine is comparable to Formula V. Formula V and 1/2/3/4/5/6 differ by the type of ascorbic compound utilized. Formula V comprises ascorbic acid/mixed ascorbates as shown in Table 1. The composition 1/2/3/4/5/6 utilized in FIG. 13B comprises only ascorbic acid and not the mixed ascorbates as shown in Table 4.

Each of the six components, 1/2/3/4/5/6, appears to be required for the full desired dose-dependent suppression of neuraminidase activity in this assay. The composition of lysine/ascorbates/flavonoid glycosides/pyridoxine HCl/threonine (1/2/3/4/5) exhibited dose dependent suppression across the full range of concentrations tested. The compositions 1/2/3; 1/2/4; and 1/2/3/5 each exhibited dose dependent suppression of neuraminidase activity in this assay only at the higher concentrations tested.

We claim:
1. An antiviral supplement oral dosage form comprising a composition comprising a therapeutically effective amount of a lysine in a single dose range of from about 1,000 mg to about 5,000 mg, an ascorbic compound, a flavonoid glycoside comprising hesperidin and rutin, a threonine, a taurine and a pyridoxine.

2. The dosage form of claim 1, wherein the dosage form is in a form selected from the group consisting of powder, capsule, lozenge, troche, tablet, liquid, and caplet.

3. The dosage form of claim 1, wherein the dosage form is a solid dosage form.

4. The dosage form of claim 1, wherein the dosage form is a chewable form.

5. The dosage form of claim 1, wherein the dosage form is a divided dosage form, wherein one dose consists of a multiplicity of units of a solid, semi-solid, or lyophilized powder dosage form.

6. The dosage form of claim 1, wherein the lysine is selected from L-lysine, L-lysine monohydrochloride, L-lysine dihydrochloride, L-lysine succinate, L-lysine glutamate, and L-lysine orotate.

7. The dosage form of claim 1, wherein the ascorbic compound is selected from one or more of ascorbic acid, calcium ascorbate, magnesium ascorbate, potassium ascorbate, sodium ascorbate, manganese ascorbate, zinc ascorbate, iron ascorbate, copper ascorbate, boron ascorbate, molybdenum ascorbate, chromium ascorbate, ascorbyl palmitate, ascorbyl arachidonate, ascorbyl stearate, ascorbyllinoleate, ascorbyl linoleneate, and ascorbyl oleate.

8. The dosage form of claim 1, wherein the flavonoid glycoside comprises hesperidin and rutin in a 1:1 weight ratio.

9. The dosage form of claim 1, wherein the pyridoxine is pyridoxine hydrochloride.

10. The dosage form of claim 1, wherein the composition comprises L-lysine monohydrochloride, ascorbic acid, hesperidin, rutin, threonine, taurine, and pyridoxine hydrochloride.

11. The dosage form of claim 10, wherein the composition further comprising an additional ascorbic compound selected from the group consisting of calcium ascorbate, niacinamide ascorbate, and ascorbyl palmitate.

12. The dosage form of claim 1, wherein the dosage form further comprises an additive selected from the group consisting of vehicle, binder, disintegrating agent, lubricant, thickener, surfactant, osmotic pressure regulator, electrolyte, sweetener, flavoring, perfume, pigment, and pH regulator.

13. The dosage form of claim 11, wherein the disintegrating agent is selected from the group consisting of microcrystalline cellulose, carboxymethylcellulose (CMC), CMC-Na, CMC-Ca, and croscarmellose sodium.

14. The dosage form of claim 12, wherein the lubricant is selected from the group consisting of leucine, isoleucine, valine, sugar-ester, hardening oil, stearic acid, magnesium stearate, talc, and macrogol.

15. The dosage form of claim 12, wherein the sweetener is selected from the group consisting of glucose, fructose, maltose, sucrose, xylose, lactose, xylitol, sorbitol, mannitol, maltitol, xylitol, coupling sugar, paratinose, glycerin, erythritol, dextrin, cyclodextrin, fructo-oligosaccharide, galacto-oligosaccharide, lacto-sucrose, thaumatin, *stevia*, *stevia* extract, rebaudioside A, glycyrrhizinic acid, saccharin, alitame, and aspartame.

16. The dosage form of claim 1, wherein a single dose comprises from about 2 g to about 3.5 g L-lysine monohydrochloride; from about 0.1 g to about 1.5 g ascorbic acid; from about 0.2 g to about 0.8 g hesperidin; from about 0.1 g to about 0.5 g rutin; from about 0.04 g to about 0.08 g pyridoxine hydrochloride; from about 0.01 g to about 0.08 g threonine; and from about 0.02 g to about 0.4 g taurine.

17. The dosage form of claim 16, further comprising from about 0.5 g to about 0.75 g calcium ascorbate; from about 0.1 g to about 0.5 g niacinamide ascorbate; and from about 0.01 g to about 0.1 g ascorbyl palmitate.

18. The dosage form of claim 2, wherein the dosage form is in a form of a tablet.

19. The dosage form of claim 18, wherein the tablet is selected from an orally disintegrable form, chewable form, effervescent form, slow release form, or immediate release form.

20. The dosage form of claim 18, wherein the tablet comprises L-lysine monohydrochloride, ascorbic acid, hesperidin, rutin, threonine, taurine, and pyridoxine hydrochloride.

21. The dosage form of claim 2, wherein the dosage form is in a form of a capsule.

* * * * *